United States Patent
Watt

(10) Patent No.: US 6,825,337 B2
(45) Date of Patent: Nov. 30, 2004

(54) ANTISENSE MODULATION OF PLML EXPRESSION

(75) Inventor: Andrew T. Watt, Vista, CA (US)

(73) Assignee: ISIS Pharmaceuticals, Inc., Carlsbad, CA (US)

(*) Notice: Subject to any disclaimer, the term of this patent is extended or adjusted under 35 U.S.C. 154(b) by 0 days.

(21) Appl. No.: 10/160,792

(22) Filed: May 31, 2002

(65) Prior Publication Data

US 2003/0225014 A1 Dec. 4, 2003

(51) Int. Cl.[7] .................. C12N 15/85; A61K 48/00; C12Q 1/68; C07H 21/04
(52) U.S. Cl. ............... 536/24.5; 536/23.1; 536/24.3; 536/24.33; 435/6; 435/375
(58) Field of Search ................ 514/44; 435/6, 435/91.1, 325, 375; 536/24.5, 23.1, 24.3, 24.1

(56) References Cited

U.S. PATENT DOCUMENTS

| | | | |
|---|---|---|---|
| 5,728,579 A | | 3/1998 | Morrison et al. ........... 435/325 |
| 5,801,154 A | * | 9/1998 | Baracchini et al. ........... 514/44 |
| 5,919,655 A | * | 7/1999 | Bandman et al. .......... 435/69.1 |
| 6,596,490 B2 | * | 7/2003 | Dattagupta ..................... 435/6 |

OTHER PUBLICATIONS

J Moran et al.,Biochimica et Biophysica Acta,"Reduction of phospholemman expression decreases osmosensitive taurine efflux in astrocyes," 2001, 1538, pp. 313–320.*
BW Morrison et al., Journal of Biological Chemistry, "Mat–8, a Novel Phospholemman–like Protein Expressed in Human Breast Tumors, Induces a Chloride Conductance in Xenopus Oocytes," 1995, vol. 270, No. 5, pp. 2176–2182.*
H Fritz et al.,Journal of Colloid and Interface Science, "Cationic Polystyrene Nanoparticles: Preparation and Characterization of a Model Drug Carrier System for Antisense Oligonucleotides,"1997, 195, pp. 272–288.*

Chen et al., Characterization of the human and rat phospholemman (PLM) cDNAs and localization of the human PLM gene to chromosome 19q13.1, Genomics, 1997, 41:435–443.

Moorman et al., Phospholemman expression induces a hyperpolarization–activated chloride current in Xenopus oocytes, J. Biol. Chem., 1992, 267:14551–14554.

Morrison et al., neu and ras initiate murine mammary tumors that share genetic markers generally absent in c–myc and int–2–initiated tumors, Oncogene, 1994, 9:3417–3426.

Morrison et al., Mat–8, a novel phospholemman–like protein expressed in human breast tumors, induces a chloride conductance in Xenopus oocytes, J. Biol. Chem., 1995, 270:2176–2182.

Nilius et al., Volume–activated Cl– channels, Gen. Pharmacol., 1996, 27:1131–1140.

O'Neill, Physiological significance of volume–regulatory transporters, Am. J. Physiol., 1999, 276:C995–C1011.

Palmer et al., Purification and complete sequence determination of the major plasma membrane substrate for cAMP–dependent protein kinase and protein kinase C in myocardium, J .Biol. Chem., 1991, 266:11126–11130.

Sweadner et al., The FXYD gene family of small ion transport regulators or channels: cDNA sequence, protein signature sequence, and expression, Genomics, 2000, 68:41–56.

* cited by examiner

Primary Examiner—John L. LeGuyader
Assistant Examiner—Terra C. Gibbs
(74) Attorney, Agent, or Firm—Licata & Tyrrell P.C.

(57) ABSTRACT

Antisense compounds, compositions and methods are provided for modulating the expression of PLML. The compositions comprise antisense compounds, particularly antisense oligonucleotides, targeted to nucleic acids encoding PLML. Methods of using these compounds for modulation of PLML expression and for treatment of diseases associated with expression of PLML are provided.

10 Claims, No Drawings

SEQUENCE LISTING

<160> NUMBER OF SEQ ID NOS: 136

<210> SEQ ID NO 1
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 1
tccgtcatcg ctcctcaggg                                              20

<210> SEQ ID NO 2
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 2
atgcattctg cccccaagga                                              20

<210> SEQ ID NO 3
<211> LENGTH: 1460
<212> TYPE: DNA
<213> ORGANISM: Homo sapiens
<220> FEATURE:
<221> NAME/KEY: CDS
<222> LOCATION: (260)...(595)

<400> SEQUENCE: 3

```
gttctccaca actgccagca atccttccac caggcaaaac acatcatcta aggaaaagaa      60
gtgaggtttg cttagggcgt ggcagcttcg gataaacgca ggactccgcc tggcagcccg     120
atttctcccg gaacctctgc tcagcctggt gaaccacaca ggcccgagtt tcacccagtc     180
cccactccac ggtgcagctg cggcttatct ctcagcccag cgagatgcca gccttcctgt     240
cccgggccag cgctctgac atg cag aag gtg acc ctg ggc ctg ctt gtg ttc      292
                     Met Gln Lys Val Thr Leu Gly Leu Leu Val Phe
                       1               5                  10 ctg gca ggc ttt cct gtc ctg gac gcc aat gac cta gaa gat aaa aac       340
Leu Ala Gly Phe Pro Val Leu Asp Ala Asn Asp Leu Glu Asp Lys Asn
             15                  20                  25 agt cct ttc tac tat gac tgg cac cag gtt ggc ggg ctc atc tgc gct       388
Ser Pro Phe Tyr Tyr Asp Trp His Gln Val Gly Gly Leu Ile Cys Ala
         30                  35                  40 ggg gtt ctg tgc gcc atg ggc atc atc atc gtc atg agt gag tgg agg       436
Gly Val Leu Cys Ala Met Gly Ile Ile Ile Val Met Ser Glu Trp Arg
     45                  50                  55 agc tcg ggg gag cag gcg ggc cgg ggc tgg ggc tcc cct ccc ctg acc       484
Ser Ser Gly Glu Gln Ala Gly Arg Gly Trp Gly Ser Pro Pro Leu Thr
 60                  65                  70                  75 act cag ctc tcc cca aca ggt gca aaa tgc aaa tgc aag ttt ggc cag       532
Thr Gln Leu Ser Pro Thr Gly Ala Lys Cys Lys Cys Lys Phe Gly Gln
                 80                  85                  90 aag tcc ggt cac cat cca ggg gag act cca cct ctc atc acc ccc ggc       580
Lys Ser Gly His His Pro Gly Glu Thr Pro Pro Leu Ile Thr Pro Gly
             95                 100                 105
```

```
tca gcc caa agc tga tgaggacaga ccagctgaaa ttgggtggag gaccgttctc    635
Ser Ala Gln Ser *
        110 tgtccccagg tcctgtctct gcacagaaac ttgaactcca ggatggaatt cttcctcctc    695 tgctgggact cctttgcatg gcagggcctc atctcacctc tcgcaagagg gtctctttgt    755 tcaattttt tttatctaaa atgattgtgc ctctgcccaa gcagcctgga gacttcctat    815 gtgtgcattg gggtggggct tggggcacca tgagaaggtt ggcgtgccct ggaggctgac    875 acagaggctg gcactgagcc tgcttgttgg gaaaagccca caggcctgtt cccttgtggc    935 ttgggacatg gcacaggccc gccctctgcc tcctcagcca tggacctca tatgcaattt    995 gggatttact agtagccaaa aggaatgaaa gagagctcta accagatgga acactggaac    1055 attccagtgg accctggacc attccaggaa aactgggaca taggatcgtc ccgctatgat    1115 ggaagtgttc agacagttta taatagtaag cccctgtgac cctctcactt accccgagac    1175 ctcactttat tacaagatct ttccaaatac ccaaatatcc ctgcaagccc gttaaataat    1235 tccctatgct acccttaata acatacaatg accacatagt gtgagaactt ccaacaagcc    1295 tcaaagtccc ttgagactcc ccaataccta ataaggcatg cgaaatgttc tcatgaacta    1355 ccccacaaca cgcctaaaac tcaaaacacc caaaaatatc tcctccaatg tcctgagaca    1415 tgaacccaaa aagagaccca caataaactc gtgacttgtc ccctc    1460

<210> SEQ ID NO 4
<211> LENGTH: 19
<212> TYPE: DNA
<213> ORGANISM: Artificial Sequence
<220> FEATURE:
<223> OTHER INFORMATION: PCR Primer

<400> SEQUENCE: 4
ttgggtggag gaccgttct                                                19

<210> SEQ ID NO 5
<211> LENGTH: 24
<212> TYPE: DNA
<213> ORGANISM: Artificial Sequence
<220> FEATURE:
<223> OTHER INFORMATION: PCR Primer

<400> SEQUENCE: 5
aattccatcc tggagttcaa gttt                                          24

<210> SEQ ID NO 6
<211> LENGTH: 25
<212> TYPE: DNA
<213> ORGANISM: Artificial Sequence
<220> FEATURE:
<223> OTHER INFORMATION: PCR Probe

<400> SEQUENCE: 6
tgtccccagg tcctgtctct gcaca                                         25

<210> SEQ ID NO 7
<211> LENGTH: 19
<212> TYPE: DNA
<213> ORGANISM: Artificial Sequence
<220> FEATURE:
<223> OTHER INFORMATION: PCR Primer

<400> SEQUENCE: 7
gaaggtgaag gtcggagtc                                                19
```

```
<210> SEQ ID NO 8
<211> LENGTH: 20
<212> TYPE: DNA
<213> ORGANISM: Artificial Sequence
<220> FEATURE:
<223> OTHER INFORMATION: PCR Primer

<400> SEQUENCE: 8
gaagatggtg atgggatttc                                                  20

<210> SEQ ID NO 9
<211> LENGTH: 20
<212> TYPE: DNA
<213> ORGANISM: Artificial Sequence
<220> FEATURE:
<223> OTHER INFORMATION: PCR Probe

<400> SEQUENCE: 9
caagcttccc gttctcagcc                                                  20

<210> SEQ ID NO 10
<211> LENGTH: 511
<212> TYPE: DNA
<213> ORGANISM: Homo sapiens
<220> FEATURE:
<221> NAME/KEY: CDS
<222> LOCATION: (60)...(323)
<220> FEATURE:
<221> NAME/KEY: misc_feature
LOCATION: 5   11
<223> OTHER INFORMATION: n = A,T,C or G

<400> SEQUENCE: 10
cccgatttct cccggaacct ctgctcagcc tggtgaacca cacaggccag cgctctgac       59 atg cag aag gtg acc ctg ggc ctg ctt gtg ttc ctg gca ggc ttt cct       107
Met Gln Lys Val Thr Leu Gly Leu Leu Val Phe Leu Ala Gly Phe Pro
 1               5                  10                  15 gtc ctg gac gcc aat gac cta gaa gat aaa aac agt cct ttc tac tat       155
Val Leu Asp Ala Asn Asp Leu Glu Asp Lys Asn Ser Pro Phe Tyr Tyr
            20                  25                  30 gac tgg cac agc ctc cag gtt ggc ggg ctc atc tgc gct ggg gtt ctg       203
Asp Trp His Ser Leu Gln Val Gly Gly Leu Ile Cys Ala Gly Val Leu
        35                  40                  45 tgc gcc atg ggc atc atc atc gtc atg agt gca aaa tgc aaa tgc aag       251
Cys Ala Met Gly Ile Ile Ile Val Met Ser Ala Lys Cys Lys Cys Lys
    50                  55                  60 ttt ggc cag aag tcc ggt cac cat cca ggg gag act cca cct ctc atc       299
Phe Gly Gln Lys Ser Gly His His Pro Gly Glu Thr Pro Pro Leu Ile
 65                  70                  75                  80 acc cca ggc tca gcc caa agc tga tgaggacaga ccagctgaaa ttgggtggag      353
Thr Pro Gly Ser Ala Gln Ser *
                85 gaccgttctc tgtccccagg tcctgtctct gcacagaaac ttgaactcca ggatggaatt     413 cttcctcctc tgctgggact cctttgcatg gcagggcctc atctcacctc tcgcaagagg     473 gtctctttgt tcaatttttt ttaatctaaa atgattan                             511

<210> SEQ ID NO 11
<211> LENGTH: 398
<212> TYPE: DNA
<213> ORGANISM: Homo sapiens
<220> FEATURE:
<221> NAME/KEY: misc_feature
<222> LOCATION: 373
<223> OTHER INFORMATION: n = A,T,C or G
```

```
<400> SEQUENCE: 11
ctgctgatcc tgaaattgta ccagcggcaa gatgtggcct ggaagggac tttaagttct      60 ccacaactgc cagcaatcct tccaccaggc aaaacacatc atctaaggaa aagaagtgag    120
gtttgcttag ggcgtggcag cttcggataa acgcaggact ccgcctggca gcccgatttc    180
tcccggaacc tctgctcagc ctggtgaacc acacaggcca gcgctctgac atgcagaagg    240
tgaccctggg cctgcttgtg ttcctggcag gctttcctgt cctggacgcc aatgacctag    300
aagataaaaa cagtcctttc tactatgact ggcacagcct ccaggttggc gggctcatct    360
gcgctggggt tcngtgcgcc atggcatcat catcgtca                            398

<210> SEQ ID NO 12
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 12
ttgctggcag ttgtggagaa                                                 20

<210> SEQ ID NO 13
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 13
cttgccgctg gtacaatttc                                                 20

<210> SEQ ID NO 14
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 14
gcctggtgga aggattgctg                                                 20

<210> SEQ ID NO 15
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 15
agatgatgtg ttttgcctgg                                                 20

<210> SEQ ID NO 16
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 16
agcgctggcc tgtgtggttc                                                 20
```

```
<210> SEQ ID NO 17
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 17
cttaaagtcc ccttccaggc                                               20

<210> SEQ ID NO 18
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 18
tgccacgccc taagcaaacc                                               20

<210> SEQ ID NO 19
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 19
aagctgccac gccctaagca                                               20

<210> SEQ ID NO 20
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 20
ctgcgtttat ccgaagctgc                                               20

<210> SEQ ID NO 21
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 21
gtcctgcgtt tatccgaagc                                               20

<210> SEQ ID NO 22
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 22
ggagtcctgc gtttatccga                                               20

<210> SEQ ID NO 23
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 23
ccaggcggag tcctgcgttt                                          20

<210> SEQ ID NO 24
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 24
cagaggttcc gggagaaatc                                          20

<210> SEQ ID NO 25
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 25
gtggttcacc aggctgagca                                          20

<210> SEQ ID NO 26
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 26
cctgtgtggt tcaccaggct                                          20

<210> SEQ ID NO 27
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 27
tcgggcctgt gtggttcacc                                          20

<210> SEQ ID NO 28
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 28
aaactcgggc ctgtgtggtt                                          20

<210> SEQ ID NO 29
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 29
taagccgcag ctgcaccgtg                                          20
```

```
<210> SEQ ID NO 30
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 30
gagcgctggc ctgtgtggtt                                              20

<210> SEQ ID NO 31
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 31
gcattttgca ctcatgacga                                              20

<210> SEQ ID NO 32
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 32
accttctgca tgtcagagcg                                              20

<210> SEQ ID NO 33
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 33
tccaggacag gaaagcctgc                                              20

<210> SEQ ID NO 34
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 34
tgccagtcat agtagaaagg                                              20

<210> SEQ ID NO 35
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 35
gcagatgagc ccgccaacct                                              20

<210> SEQ ID NO 36
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 36
ccagcgcaga tgagcccgcc                                               20

<210> SEQ ID NO 37
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 37
tgatgatgcc catggcgcac                                               20

<210> SEQ ID NO 38
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 38
catgacgatg atgatgccca                                               20

<210> SEQ ID NO 39
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 39
tccactcact catgacgatg                                               20

<210> SEQ ID NO 40
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 40
aaacttgcat ttgcattttg                                               20

<210> SEQ ID NO 41
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 41
ggacttctgg ccaaacttgc                                               20

<210> SEQ ID NO 42
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 42
ccggacttct ggccaaactt                                               20
```

<210> SEQ ID NO 43
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 43
tggatggtga ccggacttct                    20

<210> SEQ ID NO 44
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 44
gtggagtctc ccctggatgg                    20

<210> SEQ ID NO 45
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 45
gatgagaggt ggagtctccc                    20

<210> SEQ ID NO 46
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 46
ctgtcctcat cagctttggg                    20

<210> SEQ ID NO 47
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 47
tccacccaat ttcagctggt                    20

<210> SEQ ID NO 48
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 48
tcaagtttct gtgcagagac                    20

<210> SEQ ID NO 49
<211> LENGTH: 20
<212> TYPE: DNA
<213> ORGANISM: Artificial Sequence
<220> FEATURE:
<223> OTHER INFORMATION: Antisense Oligonucleotide

```
<400> SEQUENCE: 49
ccagcagagg aggaagaatt                                        20

<210> SEQ ID NO 50
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 50
tgcaaaggag tcccagcaga                                        20

<210> SEQ ID NO 51
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 51
gagatgaggc cctgccatgc                                        20

<210> SEQ ID NO 52
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 52
gaggtgagat gaggccctgc                                        20

<210> SEQ ID NO 53
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 53
gaacaaagag accctcttgc                                        20

<210> SEQ ID NO 54
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 54
aattgaacaa agagaccctc                                        20

<210> SEQ ID NO 55
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 55
ggcacaatca ttttagataa                                        20
```

```
<210> SEQ ID NO 56
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 56
tgggcagagg cacaatcatt                                               20

<210> SEQ ID NO 57
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 57
ctgctttggc agaggcacaa                                               20

<210> SEQ ID NO 58
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 58
ccccaatgca cacataggaa                                               20

<210> SEQ ID NO 59
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 59
ctccagggca cgccaacctt                                               20

<210> SEQ ID NO 60
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 60
tcagtgccag cctctgtgtc                                               20

<210> SEQ ID NO 61
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 61
ggctcagtgc cagcctctgt                                               20

<210> SEQ ID NO 62
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 62
ccacaaggga acaggcctgt                                               20

<210> SEQ ID NO 63
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 63
ccatgtccca agccacaagg                                               20

<210> SEQ ID NO 64
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 64
catatgaggt cccatggctg                                               20

<210> SEQ ID NO 65
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 65
attgcatatg aggtcccatg                                               20

<210> SEQ ID NO 66
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 66
aaatcccaaa ttgcatatga                                               20

<210> SEQ ID NO 67
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 67
ggctactagt aaatcccaaa                                               20

<210> SEQ ID NO 68
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 68
cttttggcta ctagtaaatc                                               20
```

```
<210> SEQ ID NO 69
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 69
gtgttccatc tggttagagc                                               20

<210> SEQ ID NO 70
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 70
gggtccactg gaatgttcca                                               20

<210> SEQ ID NO 71
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 71
gtccagggtc cactggaatg                                               20

<210> SEQ ID NO 72
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 72
ctggaatggt ccagggtcca                                               20

<210> SEQ ID NO 73
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 73
atgtcccagt tttcctggaa                                               20

<210> SEQ ID NO 74
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 74
cttccatcat agcgggacga                                               20

<210> SEQ ID NO 75
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 75
aactgtctga acacttccat                                          20

<210> SEQ ID NO 76
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 76
tactattata aactgtctga                                          20

<210> SEQ ID NO 77
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 77
gtaagtgaga gggtcacagg                                          20

<210> SEQ ID NO 78
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 78
tcttgtaata aagtgaggtc                                          20

<210> SEQ ID NO 79
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 79
gtagcatagg gaattattta                                          20

<210> SEQ ID NO 80
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 80
ggtcattgta tgttattaag                                          20

<210> SEQ ID NO 81
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 81
gtctcaaggg actttgaggc                                          20
```

```
<210> SEQ ID NO 82
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 82
agaacatttc gcatgcctta                                              20

<210> SEQ ID NO 83
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 83
atgagaacat ttcgcatgcc                                              20

<210> SEQ ID NO 84
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 84
gggtgttttg agttttaggc                                              20

<210> SEQ ID NO 85
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 85
tgtctcagga cattggagga                                              20

<210> SEQ ID NO 86
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 86
gttcatgtct caggacattg                                              20

<210> SEQ ID NO 87
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 87
ttttgggttc atgtctcagg                                              20

<210> SEQ ID NO 88
<211> LENGTH: 20
<212> TYPE: DNA
<213> ORGANISM: Artificial Sequence
<220> FEATURE:
<223> OTHER INFORMATION: Antisense Oligonucleotide
```

```
<400> SEQUENCE: 88
tcacgagttt attgtgggtc                                              20

<210> SEQ ID NO 89
<211> LENGTH: 20
<212> TYPE: DNA
<213> ORGANISM: Artificial Sequence
<220> FEATURE:
<223> OTHER INFORMATION: Antisense Oligonucleotide

<400> SEQUENCE: 89
acaagtcacg agtttattgt                                              20

<210> SEQ ID NO 90
<211> LENGTH: 20
<212> TYPE: DNA
<213> ORGANISM: Homo sapiens

<400> SEQUENCE: 90
gaaccacaca ggccagcgct                                              20

<210> SEQ ID NO 91
<211> LENGTH: 20
<212> TYPE: DNA
<213> ORGANISM: Homo sapiens

<400> SEQUENCE: 91
gatttctccc ggaacctctg                                              20

<210> SEQ ID NO 92
<211> LENGTH: 20
<212> TYPE: DNA
<213> ORGANISM: Homo sapiens

<400> SEQUENCE: 92
tgctcagcct ggtgaaccac                                              20

<210> SEQ ID NO 93
<211> LENGTH: 20
<212> TYPE: DNA
<213> ORGANISM: Homo sapiens

<400> SEQUENCE: 93
agcctggtga accacacagg                                              20

<210> SEQ ID NO 94
<211> LENGTH: 20
<212> TYPE: DNA
<213> ORGANISM: Homo sapiens

<400> SEQUENCE: 94
ggtgaaccac acaggcccga                                              20

<210> SEQ ID NO 95
<211> LENGTH: 20
<212> TYPE: DNA
<213> ORGANISM: Homo sapiens

<400> SEQUENCE: 95
aaccacacag gcccgagttt                                              20
```

```
<210> SEQ ID NO 96
<211> LENGTH: 20
<212> TYPE: DNA
<213> ORGANISM: Homo sapiens

<400> SEQUENCE: 96
cacggtgcag ctgcggctta                                              20

<210> SEQ ID NO 97
<211> LENGTH: 20
<212> TYPE: DNA
<213> ORGANISM: Homo sapiens

<400> SEQUENCE: 97
aaccacacag gccagcgctc                                              20

<210> SEQ ID NO 98
<211> LENGTH: 20
<212> TYPE: DNA
<213> ORGANISM: Homo sapiens

<400> SEQUENCE: 98
tcgtcatgag tgcaaaatgc                                              20

<210> SEQ ID NO 99
<211> LENGTH: 20
<212> TYPE: DNA
<213> ORGANISM: Homo sapiens

<400> SEQUENCE: 99
cgctctgaca tgcagaaggt                                              20

<210> SEQ ID NO 100
<211> LENGTH: 20
<212> TYPE: DNA
<213> ORGANISM: Homo sapiens

<400> SEQUENCE: 100
gcaggctttc ctgtcctgga                                              20

<210> SEQ ID NO 101
<211> LENGTH: 20
<212> TYPE: DNA
<213> ORGANISM: Homo sapiens

<400> SEQUENCE: 101
cctttctact atgactggca                                              20

<210> SEQ ID NO 102
<211> LENGTH: 20
<212> TYPE: DNA
<213> ORGANISM: Homo sapiens

<400> SEQUENCE: 102
aggttggcgg gctcatctgc                                              20

<210> SEQ ID NO 103
<211> LENGTH: 20
<212> TYPE: DNA
<213> ORGANISM: Homo sapiens

<400> SEQUENCE: 103
ggcgggctca tctgcgctgg                                              20
```

```
<210> SEQ ID NO 104
<211> LENGTH: 20
<212> TYPE: DNA
<213> ORGANISM: Homo sapiens

<400> SEQUENCE: 104
gtgcgccatg ggcatcatca                                          20

<210> SEQ ID NO 105
<211> LENGTH: 20
<212> TYPE: DNA
<213> ORGANISM: Homo sapiens

<400> SEQUENCE: 105
tgggcatcat catcgtcatg                                          20

<210> SEQ ID NO 106
<211> LENGTH: 20
<212> TYPE: DNA
<213> ORGANISM: Homo sapiens

<400> SEQUENCE: 106
catcgtcatg agtgagtgga                                          20

<210> SEQ ID NO 107
<211> LENGTH: 20
<212> TYPE: DNA
<213> ORGANISM: Homo sapiens

<400> SEQUENCE: 107
caaaatgcaa atgcaagttt                                          20

<210> SEQ ID NO 108
<211> LENGTH: 20
<212> TYPE: DNA
<213> ORGANISM: Homo sapiens

<400> SEQUENCE: 108
gcaagtttgg ccagaagtcc                                          20

<210> SEQ ID NO 109
<211> LENGTH: 20
<212> TYPE: DNA
<213> ORGANISM: Homo sapiens

<400> SEQUENCE: 109
aagtttggcc agaagtccgg                                          20

<210> SEQ ID NO 110
<211> LENGTH: 20
<212> TYPE: DNA
<213> ORGANISM: Homo sapiens

<400> SEQUENCE: 110
agaagtccgg tcaccatcca                                          20

<210> SEQ ID NO 111
<211> LENGTH: 20
<212> TYPE: DNA
<213> ORGANISM: Homo sapiens

<400> SEQUENCE: 111
ccatccaggg gagactccac                                          20
```

```
<210> SEQ ID NO 112
<211> LENGTH: 20
<212> TYPE: DNA
<213> ORGANISM: Homo sapiens

<400> SEQUENCE: 112
gggagactcc acctctcatc                                          20

<210> SEQ ID NO 113
<211> LENGTH: 20
<212> TYPE: DNA
<213> ORGANISM: Homo sapiens

<400> SEQUENCE: 113
cccaaagctg atgaggacag                                          20

<210> SEQ ID NO 114
<211> LENGTH: 20
<212> TYPE: DNA
<213> ORGANISM: Homo sapiens

<400> SEQUENCE: 114
accagctgaa attgggtgga                                          20

<210> SEQ ID NO 115
<211> LENGTH: 20
<212> TYPE: DNA
<213> ORGANISM: Homo sapiens

<400> SEQUENCE: 115
gtctctgcac agaaacttga                                          20

<210> SEQ ID NO 116
<211> LENGTH: 20
<212> TYPE: DNA
<213> ORGANISM: Homo sapiens

<400> SEQUENCE: 116
aattcttcct cctctgctgg                                          20

<210> SEQ ID NO 117
<211> LENGTH: 20
<212> TYPE: DNA
<213> ORGANISM: Homo sapiens

<400> SEQUENCE: 117
tctgctggga ctcctttgca                                          20

<210> SEQ ID NO 118
<211> LENGTH: 20
<212> TYPE: DNA
<213> ORGANISM: Homo sapiens

<400> SEQUENCE: 118
gcatggcagg gcctcatctc                                          20

<210> SEQ ID NO 119
<211> LENGTH: 20
<212> TYPE: DNA
<213> ORGANISM: Homo sapiens

<400> SEQUENCE: 119
gcagggcctc atctcacctc                                          20
```

```
<210> SEQ ID NO 120
<211> LENGTH: 20
<212> TYPE: DNA
<213> ORGANISM: Homo sapiens

<400> SEQUENCE: 120
gcaagagggt ctctttgttc                                               20

<210> SEQ ID NO 121
<211> LENGTH: 20
<212> TYPE: DNA
<213> ORGANISM: Homo sapiens

<400> SEQUENCE: 121
gagggtctct ttgttcaatt                                               20

<210> SEQ ID NO 122
<211> LENGTH: 20
<212> TYPE: DNA
<213> ORGANISM: Homo sapiens

<400> SEQUENCE: 122
ttatctaaaa tgattgtgcc                                               20

<210> SEQ ID NO 123
<211> LENGTH: 20
<212> TYPE: DNA
<213> ORGANISM: Homo sapiens

<400> SEQUENCE: 123
aatgattgtg cctctgccca                                               20

<210> SEQ ID NO 124
<211> LENGTH: 20
<212> TYPE: DNA
<213> ORGANISM: Homo sapiens

<400> SEQUENCE: 124
ttgtgcctct gcccaagcag                                               20

<210> SEQ ID NO 125
<211> LENGTH: 20
<212> TYPE: DNA
<213> ORGANISM: Homo sapiens

<400> SEQUENCE: 125
ttcctatgtg tgcattgggg                                               20

<210> SEQ ID NO 126
<211> LENGTH: 20
<212> TYPE: DNA
<213> ORGANISM: Homo sapiens

<400> SEQUENCE: 126
aaggttggcg tgccctggag                                               20

<210> SEQ ID NO 127
<211> LENGTH: 20
<212> TYPE: DNA
<213> ORGANISM: Homo sapiens

<400> SEQUENCE: 127
acagaggctg gcactgagcc                                               20
```

<210> SEQ ID NO 128
<211> LENGTH: 20
<212> TYPE: DNA
<213> ORGANISM: Homo sapiens

<400> SEQUENCE: 128
tttgggattt actagtagcc                                        20

<210> SEQ ID NO 129
<211> LENGTH: 20
<212> TYPE: DNA
<213> ORGANISM: Homo sapiens

<400> SEQUENCE: 129
tggaacattc cagtggaccc                                        20

<210> SEQ ID NO 130
<211> LENGTH: 20
<212> TYPE: DNA
<213> ORGANISM: Homo sapiens

<400> SEQUENCE: 130
tggaccctgg accattccag                                        20

<210> SEQ ID NO 131
<211> LENGTH: 20
<212> TYPE: DNA
<213> ORGANISM: Homo sapiens

<400> SEQUENCE: 131
tcgtcccgct atgatggaag                                        20

<210> SEQ ID NO 132
<211> LENGTH: 20
<212> TYPE: DNA
<213> ORGANISM: Homo sapiens

<400> SEQUENCE: 132
gcctcaaagt cccttgagac                                        20

<210> SEQ ID NO 133
<211> LENGTH: 20
<212> TYPE: DNA
<213> ORGANISM: Homo sapiens

<400> SEQUENCE: 133
taaggcatgc gaaatgttct                                        20

<210> SEQ ID NO 134
<211> LENGTH: 20
<212> TYPE: DNA
<213> ORGANISM: Homo sapiens

<400> SEQUENCE: 134
ggcatgcgaa atgttctcat                                        20

<210> SEQ ID NO 135
<211> LENGTH: 20
<212> TYPE: DNA
<213> ORGANISM: Homo sapiens

<400> SEQUENCE: 135
caatgtcctg agacatgaac                                        20

-continued

```
<210> SEQ ID NO 136
<211> LENGTH: 20
<212> TYPE: DNA
<213> ORGANISM: Homo sapiens

<400> SEQUENCE: 136
cctgagacat gaacccaaaa                                           20
```

ANTISENSE MODULATION OF PLML EXPRESSION

FIELD OF THE INVENTION

The present invention provides compositions and methods for modulating the expression of PLML. In particular, this invention relates to compounds, particularly oligonucleotides, specifically hybridizable with nucleic acids encoding PLML. Such compounds have been shown to modulate the expression of PLML.

BACKGROUND OF THE INVENTION

Despite the relatively constant osmolarity in mammals, volume-regulatory transporters have important roles in mammalian physiology because changes in cell volume also serve to signal cell growth and differentiation (O'Neill, *Am. J. Physiol.*, 1999, 276, C995–C1011). An increase in cell volume in mammals is the signal for activation of chloride currents mediated by volume-activated chloride channels (Nilius et al., *Gen. Pharmacol.*, 1996, 27, 1131–1140).

One such chloride channel is phospholemman, a small transmembrane protein first discovered in canine cardiac sarcolemmal vesicles in 1991 (Palmer et al., *J. Biol. Chem.*, 1991, 266, 11126–11130). Human phospholemman has since been found to be widely distributed in human tissues with the highest expression in skeletal muscle and heart, suggesting a functional role in muscle contraction (Chen et al., *Genomics*, 1997, 41, 435–443). Phospholemman's role as a chloride channel was suggested following the observation that phospholemman expression in Xenopus oocytes induces a chloride-selective current (Moorman et al., *J. Biol. Chem.*, 1992, 267, 14551–14554).

Shortly thereafter, a protein with a sequence related to phospholemman was discovered in murine mammary tumors whose expression is initiated by the transgenic oncogenes c-neu and v-Ha-Ras but not c-myc (Morrison and Leder, *Oncogene*, 1994, 9, 3417–3426). Subsequently, this phospholemman-like protein was found to be expressed in human breast tumors and, like phospholemman, can induce chloride conductance when expressed in Xenopus oocytes. This indicates a role for the phospholemman-like protein in regulation of chloride flux as a chloride channel or channel regulator (Morrison et al., *J. Biol. Chem.*, 1995, 270, 2176–2182).

The phospholemman-like protein expressed in breast tumors (PLML) is also known as mat-8 (mammary tumor, 8 KDa). In addition, it was recently named FXYD3 to highlight its classification as a member of the FXYD gene family of small ion transport channels or regulators named in recognition of the invariant amino acid residues Phe-X-Tyr-Asp in the signature motif (Sweadner and Rael, *Genomics*, 2000, 68, 41–56).

Since PLML is a marker specific for tumor cells transformed by Neu or Ras, it may be a required component for Neu and Ras transformation and its expression and function critical for maintenance of the transformed state (Morrison and Leder, *Oncogene*, 1994, 9, 3417–3426; Morrison et al., *J. Biol. Chem.*, 1995, 270, 2176–2182). If PLML function is found to be a critical component of certain classes of oncogenic events, it may prove to be an ideal target for therapeutic intervention in treatment of breast cancer because it is clear that PLML is not expressed by all cell types and thus does not perform a housekeeping function common to all cells (Morrison et al., *J. Biol. Chem.*, 1995, 270, 2176–2182).

The DNA sequence encoding mat-8 (PLML) is disclosed in U.S. Pat. No. 5,728,597 as are methods of detecting and treating breast cancer (Morrison and Leder, 1998).

Antisense technology is emerging as an effective means of reducing the expression of specific gene products and may therefore prove to be uniquely useful in a number of therapeutic, diagnostic and research applications involving modulation of PLML expression.

The present invention provides compositions and methods for modulating the expression of PLML.

SUMMARY OF THE INVENTION

The present invention is directed to compounds, particularly antisense oligonucleotides, which are targeted to a nucleic acid encoding PLML, and which modulate the expression of PLML. Pharmaceutical and other compositions comprising the compounds of the invention are also provided. Further provided are methods of modulating the expression of PLML in cells or tissues comprising contacting said cells or tissues with one or more of the antisense compounds or compositions of the invention. Further provided are methods of treating an animal, particularly a human, suspected of having or being prone to a disease or condition associated with expression of PLML by administering a therapeutically or prophylactically effective amount of one or more of the antisense compounds or compositions of the invention.

DETAILED DESCRIPTION OF THE INVENTION

The present invention employs oligomeric compounds, particularly antisense oligonucleotides, for use in modulating the function of nucleic acid molecules encoding PLML, ultimately modulating the amount of PLML produced. This is accomplished by providing antisense compounds which specifically hybridize with one or more nucleic acids encoding PLML. As used herein, the terms "target nucleic acid" and "nucleic acid encoding PLML" encompass DNA encoding PLML, RNA (including pre-mRNA and mRNA) transcribed from such DNA, and also cDNA derived from such RNA. The specific hybridization of an oligomeric compound with its target nucleic acid interferes with the normal function of the nucleic acid. This modulation of function of a target nucleic acid by compounds which specifically hybridize to it is generally referred to as "antisense". The functions of DNA to be interfered with include replication and transcription. The functions of RNA to be interfered with include all vital functions such as, for example, translocation of the RNA to the site of protein translation, translocation of the RNA to sites within the cell which are distant from the site of RNA synthesis, translation of protein from the RNA, splicing of the RNA to yield one or more mRNA species, and catalytic activity which may be engaged in or facilitated by the RNA. The overall effect of such interference with target nucleic acid function is modulation of the expression of PLML. In the context of the present invention, "modulation" means either an increase (stimulation) or a decrease (inhibition) in the expression of a gene. In the context of the present invention, inhibition is the preferred form of modulation of gene expression and mRNA is a preferred target.

It is preferred to target specific nucleic acids for antisense. "Targeting" an antisense compound to a particular nucleic acid, in the context of this invention, is a multistep process. The process usually begins with the identification of a nucleic acid sequence whose function is to be modulated.

This may be, for example, a cellular gene (or mRNA transcribed from the gene) whose expression is associated with a particular disorder or disease state, or a nucleic acid molecule from an infectious agent. In the present invention, the target is a nucleic acid molecule encoding PLML. The targeting process also includes determination of a site or sites within this gene for the antisense interaction to occur such that the desired effect, e.g., detection or modulation of expression of the protein, will result. Within the context of the present invention, a preferred intragenic site is the region encompassing the translation initiation or termination codon of the open reading frame (ORF) of the gene. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon". A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation "codon" refer to the codon or codons that are used in vivo to initiate translation of an mRNA molecule transcribed from a gene encoding PLML, regardless of the sequence(s) of such codons.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "introns," which are excised from a transcript before it is translated. The remaining (and therefore translated) regions are known as "exons" and are spliced together to form a continuous mRNA sequence. mRNA splice sites, i.e., intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. mRNA transcripts produced via the process of splicing of two (or more) mRNAs from different gene sources are known as "fusion transcripts". It has also been found that introns can be effective, and therefore preferred, target regions for antisense compounds targeted, for example, to DNA or pre-mRNA.

It is also known in the art that alternative RNA transcripts can be produced from the same genomic region of DNA. These alternative transcripts are generally known as "variants". More specifically, "pre-mRNA variants" are transcripts produced from the same genomic DNA that differ from other transcripts produced from the same genomic DNA in either their start or stop position and contain both intronic and extronic regions.

Upon excision of one or more exon or intron regions or portions thereof during splicing, pre-mRNA variants produce smaller "mRNA variants". Consequently, mRNA variants are processed pre-mRNA variants and each unique pre-mRNA variant must always produce a unique mRNA variant as a result of splicing. These mRNA variants are also known as "alternative splice variants". If no splicing of the pre-mRNA variant occurs then the pre-mRNA variant is identical to the mRNA variant.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, oligonucleotides are chosen which are sufficiently complementary to the target, i.e., hybridize sufficiently well and with sufficient specificity, to give the desired effect.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the oligonucleotide and the DNA or RNA target. It is understood in the art that the sequence of an antisense compound need not be 100% complementary to that of its target nucleic acid to be specifically hybridizable.

An antisense compound is specifically hybridizable when binding of the compound to the target DNA or RNA molecule interferes with the normal function of the target DNA or RNA to cause a loss of activity, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense and other compounds of the invention, which hybridize to the target and inhibit expression of the target, are identified through experimentation, and representative sequences of these compounds are hereinbelow identified as preferred embodiments of the invention. The sites to which these preferred antisense compounds are complementary are hereinbelow referred to as "preferred target regions" and are therefore preferred sites for targeting. As used herein the term "preferred target region" is defined as at least an 8-nucleobase portion of a region of a gene that is accessible for hybridization with a complementary sequence of nucleic acid.

While the specific sequences of particular preferred target regions can be represented by the reverse complement of the antisense oligonucleotides set forth in Table 1, one of skill in the art will recognize that these serve to illustrate and describe particular embodiments within the scope of the present invention. Additional preferred target regions may be identified by one having ordinary skill.

Stretches of at least eight (8) consecutive nucleobases selected from within the illustrative preferred target regions are considered to be suitable preferred target regions as well. Also, stretches of DNA or RNA that are about 8 to about 80 consecutive nucleobases and that comprise some portion of the 5'- or 3'-terminal sequence of a preferred target region will also be considered preferred target region for purposes of this invention. Exemplary good preferred target regions include DNA or RNA sequences that comprise at least the 8 consecutive nucleobases from the 5'-terminus of one a preferred target region (the remaining nucleobases being a consecutive stretch of the same DNA or RNA beginning immediately upstream of the 5'-terminus of the preferred target region and continuing until the DNA or RNA contains about 8 to about 80 nucleobases). Similarly good preferred target regions are represented by DNA or RNA sequences that comprise at least the 8 consecutive nucleobases from the 3'-terminus of a preferred target region (the remaining nucleobases being a consecutive stretch of the same DNA or RNA beginning immediately upstream of the 3'-terminus of the preferred target region and continuing until the target site contains about 8 to about 80 nucleobases). One having skill in the art, once armed with the empirically-derived preferred target regions herein will be able, without undue experimentation, to identify further preferred target regions. In addition, one having ordinary skill in the art will also be able to identify additional compounds, including oligonucleotide probes and primers, that hybridize to these preferred target regions using techniques available to the ordinary practitioner in the art.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

For use in kits and diagnostics, the antisense compounds of the present invention, either alone or in combination with other antisense compounds or therapeutics, can be used as tools in differential and/or combinatorial analyses to elucidate expression patterns of a portion or the entire complement of genes expressed within cells and tissues.

Expression patterns within cells or tissues treated with one or more antisense compounds are compared to control cells or tissues not treated with antisense compounds and the patterns produced are analyzed for differential levels of gene expression as they pertain, for example, to disease association, signaling pathway, cellular localization, expression level, size, structure or function of the genes examined. These analyses can be performed on stimulated or unstimulated cells and in the presence or absence of other compounds which affect expression patterns.

Examples of methods of gene expression analysis known in the art include DNA arrays or microarrays (Brazma and Vilo, *FEBS Lett.*, 2000, 480, 17–24; Celis, et al., *FEBS Lett.*, 2000, 480, 2–16), SAGE (serial analysis of gene expression) (Madden, et al., *Drug Discov. Today*, 2000, 5, 415–425), READS (restriction enzyme amplification of digested cDNAs) (Prashar and Weissman, *Methods Enzymol.*, 1999, 303, 258–72), TOGA (total gene expression analysis) (Sutcliffe, et al., *Proc. Natl. Acad. Sci. U. S. A.*, 2000, 97, 1976–81), protein arrays and proteomics (Celis, et al., *FEBS Lett.*, 2000, 480, 2–16; Jungblut, et al., *Electrophoresis*, 1999, 20, 2100–10), expressed sequence tag (EST) sequencing (Celis, et al., *FEBS Lett.*, 2000, 480, 2–16; Larsson, et al., *J. Biotechnol.*, 2000, 80, 143–57), subtractive RNA fingerprinting (SuRF) (Fuchs, et al., *Anal. Biochem.*, 2000, 286, 91–98; Larson, et al., *Cytometry*, 2000, 41, 203–208), subtractive cloning, differential display (DD) (Jurecic and Belmont, *Curr. Opin. Microbiol.*, 2000, 3, 316–21), comparative genomic hybridization (Carulli, et al., *J. Cell Biochem. Suppl.*, 1998, 31, 286–96), FISH (fluorescent in situ hybridization) techniques (Going and Gusterson, *Eur. J. Cancer*, 1999, 35, 1895–904) and mass spectrometry methods (reviewed in To, *Comb. Chem. High Throughput Screen*, 2000, 3, 235–41).

The specificity and sensitivity of antisense is also harnessed by those of skill in the art for therapeutic uses. Antisense oligonucleotides have been employed as therapeutic moieties in the treatment of disease states in animals and man. Antisense oligonucleotide drugs, including ribozymes, have been safely and effectively administered to humans and numerous clinical trials are presently underway. It is thus established that oligonucleotides can be useful therapeutic modalities that can be configured to be useful in treatment regimes for treatment of cells, tissues and animals, especially humans.

In the context of this invention, the term "oligonucleotide" refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense oligonucleotides are a preferred form of antisense compound, the present invention comprehends other oligomeric antisense compounds, including but not limited to oligonucleotide mimetics such as are described below. The antisense compounds in accordance with this invention preferably comprise from about 8 to about 80 nucleobases (i.e. from about 8 to about 80 linked nucleosides). Particularly preferred antisense compounds are antisense oligonucleotides from about 8 to about 50 nucleobases, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression.

Antisense compounds 8–80 nucleobases in length comprising a stretch of at least eight (8) consecutive nucleobases selected from within the illustrative antisense compounds are considered to be suitable antisense compounds as well.

Exemplary preferred antisense compounds include DNA or RNA sequences that comprise at least the 8 consecutive nucleobases from the 5'-terminus of one of the illustrative preferred antisense compounds (the remaining nucleobases being a consecutive stretch of the same DNA or RNA beginning immediately upstream of the 5'-terminus of the antisense compound which is specifically hybridizable to the target nucleic acid and continuing until the DNA or RNA contains about 8 to about 80 nucleobases). Similarly preferred antisense compounds are represented by DNA or RNA sequences that comprise at least the 8 consecutive nucleobases from the 3'-terminus of one of the illustrative preferred antisense compounds (the remaining nucleobases being a consecutive stretch of the same DNA or RNA beginning immediately downstream of the 3'-terminus of the antisense compound which is specifically hybridizable to the target nucleic acid and continuing until the DNA or RNA contains about 8 to about 80 nucleobases). One having skill in the art, once armed with the empirically-derived preferred antisense compounds illustrated herein will be able, without undue experimentation, to identify further preferred antisense compounds.

Antisense and other compounds of the invention, which hybridize to the target and inhibit expression of the target, are identified through experimentation, and representative sequences of these compounds are herein identified as preferred embodiments of the invention. While specific sequences of the antisense compounds are set forth herein, one of skill in the art will recognize that these serve to illustrate and describe particular embodiments within the scope of the present invention. Additional preferred antisense compounds may be identified by one having ordinary skill.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn, the respective ends of this linear polymeric structure can be further joined to form a circular structure, however, open linear structures are generally preferred. In addition, linear structures may also have internal nucleobase complementarity and may therefore fold in a manner as to produce a double stranded structure. Within the oligonucleotide structure, the phosphate groups are commonly referred to as forming the internucleoside backbone of the oligonucleotide. The normal linkage or backbone of RNA and DNA is a 3' to 5' phosphodiester linkage.

Specific examples of preferred antisense compounds useful in this invention include oligonucleotides containing modified backbones or non-natural internucleoside linkages. As defined in this specification, oligonucleotides having modified backbones include those that retain a phosphorus atom in the backbone and those that do not have a phosphorus atom in the backbone. For the purposes of this specification, and as sometimes referenced in the art, modified oligonucleotides that do not have a phosphorus atom in their internucleoside backbone can also be considered to be oligonucleosides.

Preferred modified oligonucleotide backbones include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Preferred oligonucleotides having inverted polarity comprise a single 3' to 3' linkage at the 3'-most internucleotide linkage i.e. a single inverted nucleoside residue which may be abasic (the nucleobase is missing or has a hydroxyl group in place thereof). Various salts, mixed salts and free acid forms are also included.

Representative United States patents that teach the preparation of the above phosphorus-containing linkages include, but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, certain of which are commonly owned with this application, and each of which is herein incorporated by reference.

Preferred modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts.

Representative United States patents that teach the preparation of the above oligonucleosides include, but are not limited to, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, certain of which are commonly owned with this application, and each of which is herein incorporated by reference.

In other preferred oligonucleotide mimetics, both the sugar and the internucleoside linkage, i.e., the backbone, of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Representative United States patents that teach the preparation of PNA compounds include, but are not limited to, U.S. Pat. Nos. 5,539,082; 5,714,331; and 5,719,262, each of which is herein incorporated by reference. Further teaching of PNA compounds can be found in Nielsen et al., *Science*, 1991, 254, 1497–1500.

Most preferred embodiments of the invention are oligonucleotides with phosphorothioate backbones and oligonucleosides with heteroatom backbones, and in particular —$CH_2$—NH—O—$CH_2$—, —$CH_2$—N($CH_3$)—O—$CH_2$— [known as a methylene (methylimino) or MMI backbone], —$CH_2$—O—N($CH_3$)—$CH_2$—, —$CH_2$—N($CH_3$)—N($CH_3$)—$CH_2$— and —O—N($CH_3$)—$CH_2$—$CH_2$— [wherein the native phosphodiester backbone is represented as —O—P—O—$CH_2$—] of the above referenced U.S. Pat. No. 5,489,677, and the amide backbones of the above referenced U.S. Pat. No. 5,602,240. Also preferred are oligonucleotides having morpholino backbone structures of the above-referenced U.S. Pat. No. 5,034,506.

Modified oligonucleotides may also contain one or more substituted sugar moieties. Preferred oligonucleotides comprise one of the following at the 2' position: OH; F; O—, S—, or N-alkyl; O—, S—, or N-alkenyl; O—, S— or N-alkynyl; or O-alkyl-O-alkyl, wherein the alkyl, alkenyl and alkynyl may be substituted or unsubstituted $C_1$ to $C_{10}$ alkyl or $C_2$ to $C_{10}$ alkenyl and alkynyl. Particularly preferred are O[($CH_2$)$_n$O]$_m$$CH_3$, O($CH_2$)$_n$O$CH_3$, O($CH_2$)$_n$$NH_2$, O($CH_2$)$_n$$CH_3$, O($CH_2$)$_n$O$NH_2$, and O($CH_2$)$_n$ON[($CH_2$)$_n$$CH_3$]$_2$, where n and m are from 1 to about 10. Other preferred oligonucleotides comprise one of the following at the 2' position: $C_1$ to $C_{10}$ lower alkyl, substituted lower alkyl, alkenyl, alkynyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—$CH_2CH_2OCH_3$, also known as 2'-O-(2-methoxyethyl) or 2'-MOE) (Martin et al., *Helv. Chim. Acta*, 1995, 78, 486–504) i.e., an alkoxyalkoxy group. A further preferred modification includes 2'-dimethylaminooxyethoxy, i.e., a O($CH_2$)$_2$ON($CH_3$)$_2$ group, also known as 2'-DMAOE, as described in examples hereinbelow, and 2'-dimethylaminoethoxyethoxy (also known in the art as 2'-O-dimethyl-amino-ethoxy-ethyl or 2'-DMAEOE), i.e., 2'-O—$CH_2$—O—$CH_2$—N($CH_3$)$_2$, also described in examples hereinbelow.

Other preferred modifications include 2'-methoxy (2'-O—$CH_3$), 2'-aminopropoxy (2'-O$CH_2CH_2CH_2NH_2$), 2'-allyl (2'-$CH_2$—CH=$CH_2$), 2'-O-allyl (2'-O—$CH_2$—CH=$CH_2$) and 2'-fluoro (2'-F). The 2'-modification may be in the arabino (up) position or ribo (down) position. A preferred 2'-arabino modification is 2'-F. Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, certain of which are commonly owned with the instant application, and each of which is herein incorporated by reference in its entirety.

A further preferred modification includes Locked Nucleic Acids (LNAs) in which the 2'-hydroxyl group is linked to the 3' or 4' carbon atom of the sugar ring thereby forming a bicyclic sugar moiety. The linkage is preferably a methelyne (—$CH_2$—)$_n$ group bridging the 2' oxygen atom and the 4' carbon atom wherein n is 1 or 2. LNAs and preparation thereof are described in WO 98/39352 and WO 99/14226.

Oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3- d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687, 808, those disclosed in *The Concise Encyclopedia Of Polymer Science And Engineering*, pages 858–859, Kroschwitz, J. I., ed. John Wiley & Sons, 1990, those disclosed by Englisch et al., *Angewandte Chemie*, International Edition, 1991, 30, 613, and those disclosed by Sanghvi, Y. S., Chapter 15, *Antisense Research and Applications*, pages 289–302, Crooke, S. T. and Lebleu, B. ed., CRC Press, 1993. Certain of these nucleobases are particularly useful for increasing the binding affinity of the oligomeric compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6–1.2° C. (Sanghvi, Y. S., Crooke, S. T. and Lebleu, B., eds., *Antisense Research and Applications*, CRC Press, Boca Raton, 1993, pp. 276–278) and are presently preferred base substitutions, even more particularly when combined with 2'-O-methoxyethyl sugar modifications.

Representative United States patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175, 273; 5,367,066; 5,432,272; 5,457,187; 5,459,255; 5,484, 908; 5,502,177; 5,525,711; 5,552,540; 5,587,469; 5,594, 121, 5,596,091; 5,614,617; 5,645,985; 5,830,653; 5,763, 588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Another modification of the oligonucleotides of the invention involves chemically linking to the oligonucleotide one or more moieties or conjugates which enhance the activity, cellular distribution or cellular uptake of the oligonucleotide. The compounds of the invention can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmacodynamic properties of oligomers, and groups that enhance the pharmacokinetic properties of oligomers. Typical conjugate groups include cholesterols, lipids, phospholipids, biotin, phenazine, folate, phenanthridine, anthraquinone, acridine, fluoresceins, rhodamines, coumarins, and dyes. Groups that enhance the pharmacodynamic properties, in the context of this invention, include groups that improve oligomer uptake, enhance oligomer resistance to degradation, and/or strengthen sequence-specific hybridization with RNA. Groups that enhance the pharmacokinetic properties, in the context of this invention, include groups that improve oligomer uptake, distribution, metabolism or excretion. Representative conjugate groups are disclosed in International Patent Application PCT/US92/09196, filed Oct. 23, 1992 the entire disclosure of which is incorporated herein by reference. Conjugate moieties include but are not limited to lipid moieties such as a cholesterol moiety (Letsinger et al., *Proc. Natl. Acad. Sci. USA*, 1989, 86, 6553–6556), cholic acid (Manoharan et al., *Bioorg. Med. Chem. Let.*, 1994, 4, 1053–1060), a thioether, e.g., hexyl-S-tritylthiol (Manoharan et al., *Ann. N.Y. Acad. Sci.*, 1992, 660, 306–309; Manoharan et al., *Bioorg. Med. Chem. Let.*, 1993, 3, 2765–2770), a thiocholesterol (Oberhauser et al., *Nucl. Acids Res.*, 1992, 20, 533–538), an aliphatic chain, e.g., dodecandiol or undecyl residues (Saison-Behmoaras et al., *EMBO J.*, 1991, 10, 1111–1118; Kabanov et al., *FEBS Lett.*, 1990, 259, 327–330; Svinarchuk et al., *Biochimie*, 1993, 75, 49–54), a phospholipid, e.g., di-hexadecyl-rac-glycerol or triethyl-ammonium 1,2-di-O-hexadecyl-rac-glycero-3-H-phosphonate (Manoharan et al., *Tetrahedron Lett.*, 1995, 36, 3651–3654; Shea et al., *Nucl. Acids Res.*, 1990, 18, 3777–3783), a polyamine or a polyethylene glycol chain (Manoharan et al., *Nucleosides & Nucleotides*, 1995, 14, 969–973), or adamantane acetic acid (Manoharan et al., *Tetrahedron Lett.*, 1995, 36, 3651–3654), a palmityl moiety (Mishra et al., *Biochim. Biophys. Acta*, 1995, 1264, 229–237), or an octadecylamine or hexylamino-carbonyl-oxycholesterol moiety (Crooke et al., *J. Pharmacol. Exp. Ther.*, 1996, 277, 923–937). Oligonucleotides of the invention may also be conjugated to active drug substances, for example, aspirin, warfarin, phenylbutazone, ibuprofen, suprofen, fenbufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indomethicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative United States patents that teach the preparation of such oligonucleotide conjugates include, but are not limited to, U.S. Pat. Nos. 4,828,979; 4,948,882; 5,218, 105; 5,525,465; 5,541,313; 5,545,730; 5,552,538; 5,578, 717, 5,580,731; 5,580,731; 5,591,584; 5,109,124; 5,118, 802; 5,138,045; 5,414,077; 5,486,603; 5,512,439; 5,578, 718; 5,608,046; 4,587,044; 4,605,735; 4,667,025; 4,762, 779; 4,789,737; 4,824,941; 4,835,263; 4,876,335; 4,904, 582; 4,958,013; 5,082,830; 5,112,963; 5,214,136; 5,082, 830; 5,112,963; 5,214,136; 5,245,022; 5,254,469; 5,258, 506; 5,262,536; 5,272,250; 5,292,873; 5,317,098; 5,371, 241, 5,391,723; 5,416,203, 5,451,463; 5,510,475; 5,512, 667; 5,514,785; 5,565,552; 5,567,810; 5,574,142; 5,585, 481; 5,587,371; 5,595,726; 5,597,696; 5,599,923; 5,599,928 and 5,688,941, certain of which are commonly owned with the instant application, and each of which is herein incorporated by reference.

It is not necessary for all positions in a given compound to be uniformly modified, and in fact more than one of the aforementioned modifications may be incorporated in a single compound or even at a single nucleoside within an oligonucleotide. The present invention also includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit, i.e., a nucleotide in the case of an oligonucleotide compound. These oligonucleotides typically contain at least one region wherein the oligonucleotide is modified so as to confer upon the oligonucleotide increased resistance to nuclease degradation, increased cellular uptake, increased stability and/or increased binding affinity for the target nucleic acid. An additional region of the oligonucleotide may serve as a substrate for enzymes capable of cleaving RNA:DNA or RNA:RNA hybrids. By way of example, RNAse H is a cellular endonuclease which cleaves the RNA strand of an RNA:DNA duplex. Activation of RNase H, therefore, results in cleavage of the RNA target, thereby greatly enhancing the efficiency of oligonucleotide inhibition of gene expression. The cleavage of RNA:RNA hybrids can, in like fashion, be accomplished through the actions of endoribonucleases, such as interferon-induced RNAseL which cleaves both cellular and viral RNA. Consequently, comparable results can often be obtained with shorter oligonucleotides when chimeric oligonucleotides are used, compared to phosphorothioate deoxyoligonucleotides hybridizing to the same target region. Cleavage of the RNA target can be routinely detected by gel electrophoresis and, if necessary, associated nucleic acid hybridization techniques known in the art.

Chimeric antisense compounds of the invention may be formed as composite structures of two or more oligonucleotides, modified oligonucleotides, oligonucleosides and/or oligonucleotide mimetics as described above. Such compounds have also been referred to in the art as hybrids or gapmers. Representative United States patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof. Accordingly, for example, the disclosure is also drawn to prodrugs and pharmaceutically acceptable salts of the compounds of the invention, pharmaceutically acceptable salts of such prodrugs, and other bioequivalents.

The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl) phosphate] derivatives according to the methods disclosed in WO 93/24510 to Gosselin et al., published Dec. 9, 1993 or in WO 94/26764 and U.S. Pat. No. 5,770,713 to Imbach et al.

The term "pharmaceutically acceptable salts" refers to physiologically and pharmaceutically acceptable salts of the compounds of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1–19). The base addition salts of said acidic compounds are prepared by contacting the free acid form with a sufficient amount of the desired base to produce the salt in the conventional manner. The free acid form may be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the 20 alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds may also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

The antisense compounds of the present invention can be utilized for diagnostics, therapeutics, prophylaxis and as research reagents and kits. For therapeutics, an animal, preferably a human, suspected of having a disease or disorder which can be treated by modulating the expression of PLML is treated by administering antisense compounds in accordance with this invention. The compounds of the invention can be utilized in pharmaceutical compositions by adding an effective amount of an antisense compound to a suitable pharmaceutically acceptable diluent or carrier. Use of the antisense compounds and methods of the invention may also be useful prophylactically, e.g., to prevent or delay infection, inflammation or tumor formation, for example.

The antisense compounds of the invention are useful for research and diagnostics, because these compounds hybridize to nucleic acids encoding PLML, enabling sandwich and other assays to easily be constructed to exploit this fact. Hybridization of the antisense oligonucleotides of the invention with a nucleic acid encoding PLML can be detected by means known in the art. Such means may include conjugation of an enzyme to the oligonucleotide, radiolabelling of the oligonucleotide or any other suitable detection means. Kits using such detection means for detecting the level of PLML in a sample may also be prepared.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration.

Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful. Preferred topical formulations include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA). Oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters include but are not limited arachidonic acid, oleic acid, eicosanoic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a $C_{1-10}$ alkyl ester (e.g. isopropylmyristate IPM), monoglyceride, diglyceride or pharmaceutically acceptable salt thereof. Topical formulations are described in detail in U.S. patent application Ser. No. 09/315,298 filed on May 20, 1999 which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts include chenodeoxycholic acid (CDCA) and ursodeoxychenodeoxycholic acid (UDCA), cholic acid, dehydrocholic acid, deoxycholic acid, glucholic acid, glycholic acid, glycodeoxycholic acid, taurocholic acid, taurodeoxycholic acid, sodium tauro-24,25-dihydro-fusidate and sodium glycodihydrofusidate. Preferred fatty acids include arachidonic acid, undecanoic acid, oleic acid, lauric acid, caprylic acid, capric acid, myristic acid, palmitic acid, stearic acid, linoleic acid, linolenic acid, dicaprate, tricaprate, monoolein, dilaurin, glyceryl 1-monocaprate, 1-dodecylazacycloheptan-2-one, an acylcarnitine, an acylcholine, or a monoglyceride, a diglyceride or a pharmaceutically acceptable salt thereof (e.g. sodium). Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents include poly-amino acids; polyimines; polyacrylates; polyalkylacrylates, polyoxethanes, polyalkylcyanoacrylates; cationized gelatins, albumins, starches, acrylates, polyethyleneglycols (PEG) and starches; polyalkylcyanoacrylates; DEAE-derivatized polyimines, pollulans, celluloses and starches. Particularly preferred complexing agents include chitosan, N-trimethylchitosan, poly-L-lysine, polyhistidine, polyornithine, polyspermines, protamine, polyvinylpyridine, polythiodiethylaminomethylethylene P(TDAE), polyaminostyrene (e.g. p-amino), poly(methylcyanoacrylate), poly(ethylcyanoacrylate), poly(butylcyanoacrylate), poly(isobutylcyanoacrylate), poly(isohexylcynaoacrylate), DEAE-methacrylate, DEAE-hexylacrylate, DEAE-acrylamide, DEAE-albumin and DEAE-dextran, polymethylacrylate, polyhexylacrylate, poly(D,L-lactic acid), poly(DL-lactic-co-glycolic acid (PLGA), alginate, and polyethyleneglycol (PEG). Oral formulations for oligonucleotides and their preparation are described in detail in U.S. application Ser. No. 08/886,829 (filed Jul. 1, 1997), Ser. No. 09/108,673 (filed Jul. 1, 1998), Ser. No. 09/256,515 (filed Feb. 23, 1999), Ser. No. 09/082,624 (filed May 21, 1998) and Ser. No. 09/315,298 (filed May 20, 1999), each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

In one embodiment of the present invention the pharmaceutical compositions may be formulated and used as foams. Pharmaceutical foams include formulations such as, but not limited to, emulsions, microemulsions, creams, jellies and liposomes. While basically similar in nature these formulations vary in the components and the consistency of the final product. The preparation of such compositions and formulations is generally known to those skilled in the pharmaceutical and formulation arts and may be applied to the formulation of the compositions of the present invention.

Emulsions

The compositions of the present invention may be prepared and formulated as emulsions. Emulsions are typically heterogenous systems of one liquid dispersed in another in the form of droplets usually exceeding 0.1 μm in diameter (Idson, in *Pharmaceutical Dosage Forms*, Lieberman, Rieger and Banker (Eds.), 1988, Marcel Dekker, Inc., New York, N.Y., volume 1, p. 199; Rosoff, in *Pharmaceutical Dosage Forms*, Lieberman, Rieger and Banker (Eds.), 1988, Marcel Dekker, Inc., New York, N.Y., Volume 1, p. 245; Block in *Pharmaceutical Dosage Forms*, Lieberman, Rieger and Banker (Eds.), 1988, Marcel Dekker, Inc., New York, N.Y., volume 2, p. 335; Higuchi et al., in *Remington's Pharmaceutical Sciences*, Mack Publishing Co., Easton, Pa., 1985, p. 301). Emulsions are often biphasic systems comprising two immiscible liquid phases intimately mixed and dispersed with each other. In general, emulsions may be of either the water-in-oil (w/o) or the oil-in-water (o/w) variety. When an aqueous phase is finely divided into and dispersed as minute droplets into a bulk oily phase, the resulting composition is called a water-in-oil (w/o) emulsion. Alternatively, when an oily phase is finely divided into and dispersed as minute droplets into a bulk aqueous phase, the resulting composition is called an oil-in-water (o/w) emulsion. Emulsions may contain additional components in addition to the dispersed phases, and the active drug which may be present as a solution in either the aqueous phase, oily phase or itself as a separate phase. Pharmaceutical excipients such as emulsifiers, stabilizers, dyes, and anti-oxidants may also be present in emulsions as needed. Pharmaceutical emulsions may also be multiple emulsions that are comprised of more than two phases such as, for example, in the case of oil-in-water-in-oil (o/w/o) and water-in-oil-in-water (w/o/w) emulsions. Such complex formulations often provide certain advantages that simple binary emulsions do not. Multiple emulsions in which individual oil droplets of an o/w emulsion enclose small water droplets constitute a w/o/w emulsion. Likewise a system of oil droplets enclosed in globules of water stabilized in an oily continuous phase provides an o/w/o emulsion.

Emulsions are characterized by little or no thermodynamic stability. Often, the dispersed or discontinuous phase of the emulsion is well dispersed into the external or continuous phase and maintained in this form through the means of emulsifiers or the viscosity of the formulation. Either of the phases of the emulsion may be a semisolid or a solid, as is the case of emulsion-style ointment bases and creams. Other means of stabilizing emulsions entail the use of emulsifiers that may be incorporated into either phase of the emulsion. Emulsifiers may broadly be classified into four categories: synthetic surfactants, naturally occurring emulsifiers, absorption bases, and finely dispersed solids (Idson, in *Pharmaceutical Dosage Forms*, Lieberman, Rieger and Banker (Eds.), 1988, Marcel Dekker, Inc., New York, N.Y., volume 1, p. 199).

Synthetic surfactants, also known as surface active agents, have found wide applicability in the formulation of emulsions and have been reviewed in the literature (Rieger, in *Pharmaceutical Dosage Forms*, Lieberman, Rieger and Banker (Eds.), 1988, Marcel Dekker, Inc., New York, N.Y., volume 1, p. 285; Idson, in *Pharmaceutical Dosage Forms*, Lieberman, Rieger and Banker (Eds.), Marcel Dekker, Inc., New York, N.Y., 1988, volume 1, p. 199). Surfactants are typically amphiphilic and comprise a hydrophilic and a hydrophobic portion. The ratio of the hydrophilic to the hydrophobic nature of the surfactant has been termed the hydrophile/lipophile balance (HLB) and is a valuable tool in categorizing and selecting surfactants in the preparation of formulations. Surfactants may be classified into different classes based on the nature of the hydrophilic group: nonionic, anionic, cationic and amphoteric (Rieger, in *Pharmaceutical Dosage Forms*, Lieberman, Rieger and Banker (Eds.), 1988, Marcel Dekker, Inc., New York, N.Y., volume 1, p. 285).

Naturally occurring emulsifiers used in emulsion formulations include lanolin, beeswax, phosphatides, lecithin and acacia. Absorption bases possess hydrophilic properties such that they can soak up water to form w/o emulsions yet retain their semisolid consistencies, such as anhydrous lanolin and hydrophilic petrolatum. Finely divided solids have also been used as good emulsifiers especially in combination with surfactants and in viscous preparations. These include polar inorganic solids, such as heavy metal hydroxides, nonswelling clays such as bentonite, attapulgite, hectorite, kaolin, montmorillonite, colloidal aluminum silicate and colloidal magnesium aluminum silicate, pigments and nonpolar solids such as carbon or glyceryl tristearate.

A large variety of non-emulsifying materials are also included in emulsion formulations and contribute to the properties of emulsions. These include fats, oils, waxes, fatty acids, fatty alcohols, fatty esters, humectants, hydrophilic colloids, preservatives and antioxidants (Block, in *Pharmaceutical Dosage Forms*, Lieberman, Rieger and Banker (Eds.), 1988, Marcel Dekker, Inc., New York, N.Y., volume 1, p. 335; Idson, in *Pharmaceutical Dosage Forms*, Lieberman, Rieger and Banker (Eds.), 1988, Marcel Dekker, Inc., New York, N.Y., volume 1, p. 199).

Hydrophilic colloids or hydrocolloids include naturally occurring gums and synthetic polymers such as polysaccharides (for example, acacia, agar, alginic acid, carrageenan, guar gum, karaya gum, and tragacanth), cellulose derivatives (for example, carboxymethylcellulose and carboxypropylcellulose), and synthetic polymers (for example, carbomers, cellulose ethers, and carboxyvinyl polymers). These disperse or swell in water to form colloidal solutions that stabilize emulsions by forming strong interfacial films around the dispersed-phase droplets and by increasing the viscosity of the external phase.

Since emulsions often contain a number of ingredients such as carbohydrates, proteins, sterols and phosphatides that may readily support the growth of microbes, these formulations often incorporate preservatives. Commonly used preservatives included in emulsion formulations include methyl paraben, propyl paraben, quaternary ammonium salts, benzalkonium chloride, esters of p-hydroxybenzoic acid, and boric acid. Antioxidants are also commonly added to emulsion formulations to prevent deterioration of the formulation. Antioxidants used may be free radical scavengers such as tocopherols, alkyl gallates, butylated hydroxyanisole, butylated hydroxytoluene, or reducing agents such as ascorbic acid and sodium metabisulfite, and antioxidant synergists such as citric acid, tartaric acid, and lecithin.

The application of emulsion formulations via dermatological, oral and parenteral routes and methods for their manufacture have been reviewed in the literature (Idson, in *Pharmaceutical Dosage Forms*, Lieberman, Rieger and Banker (Eds.), 1988, Marcel Dekker, Inc., New York, N.Y., volume 1, p. 199). Emulsion formulations for oral delivery have been very widely used because of ease of formulation, as well as efficacy from an absorption and bioavailability standpoint (Rosoff, in *Pharmaceutical Dosage Forms*, Lieberman, Rieger and Banker (Eds.), 1988, Marcel Dekker, Inc., New York, N.Y., volume 1, p. 245; Idson, in *Pharmaceutical Dosage Forms*, Lieberman, Rieger and Banker (Eds.), 1988, Marcel Dekker, Inc., New York, N.Y., volume 1, p. 199). Mineral-oil base laxatives, oil-soluble vitamins and high fat nutritive preparations are among the materials that have commonly been administered orally as o/w emulsions.

In one embodiment of the present invention, the compositions of oligonucleotides and nucleic acids are formulated as microemulsions. A microemulsion may be defined as a system of water, oil and amphiphile which is a single optically isotropic and thermodynamically stable liquid solution (Rosoff, in *Pharmaceutical Dosage Forms*, Lieberman, Rieger and Banker (Eds.), 1988, Marcel Dekker, Inc., New York, N.Y., volume 1, p. 245). Typically microemulsions are systems that are prepared by first dispersing an oil in an aqueous surfactant solution and then adding a sufficient amount of a fourth component, generally an intermediate chain-length alcohol to form a transparent system. Therefore, microemulsions have also been described as thermodynamically stable, isotropically clear dispersions of two immiscible liquids that are stabilized by interfacial films of surface-active molecules (Leung and Shah, in: *Controlled Release of Drugs: Polymers and Aggregate Systems*, Rosoff, M., Ed., 1989, VCH Publishers, New York, pages 185–215). Microemulsions commonly are prepared via a combination of three to five components that include oil, water, surfactant, cosurfactant and electrolyte. Whether the microemulsion is of the water-in-oil (w/o) or an oil-in-water (o/w) type is dependent on the properties of the oil and surfactant used and on the structure and geometric packing of the polar heads and hydrocarbon tails of the surfactant molecules (Schott, in *Remington's Pharmaceutical Sciences*, Mack Publishing Co., Easton, Pa., 1985, p. 271).

The phenomenological approach utilizing phase diagrams has been extensively studied and has yielded a comprehensive knowledge, to one skilled in the art, of how to formulate microemulsions (Rosoff, in *Pharmaceutical Dosage Forms*, Lieberman, Rieger and Banker (Eds.), 1988, Marcel Dekker, Inc., New York, N.Y., volume 1, p. 245; Block, in *Pharmaceutical Dosage Forms*, Lieberman, Rieger and Banker (Eds.), 1988, Marcel Dekker, Inc., New York, N.Y., volume 1, p. 335). Compared to conventional emulsions, microemulsions offer the advantage of solubilizing water-insoluble drugs in a formulation of thermodynamically stable droplets that are formed spontaneously.

Surfactants used in the preparation of microemulsions include, but are not limited to, ionic surfactants, non-ionic surfactants, Brij 96, polyoxyethylene oleyl ethers, polyglycerol fatty acid esters, tetraglycerol monolaurate (ML310), tetraglycerol monooleate (MO310), hexaglycerol monooleate (PO310), hexaglycerol pentaoleate (PO500), decaglycerol monocaprate (MCA750), decaglycerol monooleate (MO750), decaglycerol sequioleate (SO750), decaglycerol decaoleate (DAO750), alone or in combination with cosurfactants. The cosurfactant, usually a short-chain alcohol such as ethanol, 1-propanol, and 1-butanol, serves to increase the interfacial fluidity by penetrating into the surfactant film and consequently creating a disordered film because of the void space generated among surfactant molecules. Microemulsions may, however, be prepared without the use of cosurfactants and alcohol-free self-emulsifying microemulsion systems are known in the art. The aqueous phase may typically be, but is not limited to, water, an aqueous solution of the drug, glycerol, PEG300, PEG400, polyglycerols, propylene glycols, and derivatives of ethylene glycol. The oil phase may include, but is not limited to, materials such as Captex 300, Captex 355, Capmul MCM, fatty acid esters, medium chain (C8–C12) mono, di, and tri-glycerides, polyoxyethylated glyceryl fatty acid esters, fatty alcohols, polyglycolized glycerides, saturated polyglycolized C8–C10 glycerides, vegetable oils and silicone oil.

Microemulsions are particularly of interest from the standpoint of drug solubilization and the enhanced absorption of drugs. Lipid based microemulsions (both o/w and w/o) have been proposed to enhance the oral bioavailability of drugs, including peptides (Constantinides et al., *Pharmaceutical Research*, 1994, 11, 1385–1390; Ritschel, *Meth. Find. Exp. Clin. Pharmacol.*, 1993, 13, 205). Microemulsions afford advantages of improved drug solubilization, protection of drug from enzymatic hydrolysis, possible enhancement of drug absorption due to surfactant-induced alterations in membrane fluidity and permeability, ease of preparation, ease of oral administration over solid dosage forms, improved clinical potency, and decreased toxicity (Constantinides et al., *Pharmaceutical Research*, 1994, 11, 1385; Ho et al., *J. Pharm. Sci.*, 1996, 85, 138–143). Often microemulsions may form spontaneously when their components are brought together at ambient temperature. This may be particularly advantageous when formulating thermolabile drugs, peptides or oligonucleotides. Microemulsions have also been effective in the transdermal delivery of active components in both cosmetic and pharmaceutical applications. It is expected that the microemulsion compositions and formulations of the present invention will facilitate the increased systemic absorption of oligonucleotides and nucleic acids from the gastrointestinal tract, as well as improve the local cellular uptake of oligonucleotides and nucleic acids within the gastrointestinal tract, vagina, buccal cavity and other areas of administration.

Microemulsions of the present invention may also contain additional components and additives such as sorbitan monostearate (Grill 3), Labrasol, and penetration enhancers to improve the properties of the formulation and to enhance the absorption of the oligonucleotides and nucleic acids of the present invention. Penetration enhancers used in the microemulsions of the present invention may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Each of these classes has been discussed above.

Liposomes

There are many organized surfactant structures besides microemulsions that have been studied and used for the formulation of drugs. These include monolayers, micelles, bilayers and vesicles. Vesicles, such as liposomes, have attracted great interest because of their specificity and the duration of action they offer from the standpoint of drug delivery. As used in the present invention, the term "liposome" means a vesicle composed of amphiphilic lipids arranged in a spherical bilayer or bilayers.

Liposomes are unilamellar or multilamellar vesicles which have a membrane formed from a lipophilic material and an aqueous interior. The aqueous portion contains the composition to be delivered. Cationic liposomes possess the advantage of being able to fuse to the cell wall. Non-cationic liposomes, although not able to fuse as efficiently with the cell wall, are taken up by macrophages in vivo.

In order to cross intact mammalian skin, lipid vesicles must pass through a series of fine pores, each with a diameter less than 50 nm, under the influence of a suitable transdermal gradient. Therefore, it is desirable to use a liposome which is highly deformable and able to pass through such fine pores.

Further advantages of liposomes include; liposomes obtained from natural phospholipids are biocompatible and biodegradable; liposomes can incorporate a wide range of water and lipid soluble drugs; liposomes can protect encapsulated drugs in their internal compartments from metabolism and degradation (Rosoff, in *Pharmaceutical Dosage Forms*, Lieberman, Rieger and Banker (Eds.), 1988, Marcel Dekker, Inc., New York, N.Y., volume 1, p. 245). Important considerations in the preparation of liposome formulations are the lipid surface charge, vesicle size and the aqueous volume of the liposomes.

Liposomes are useful for the transfer and delivery of active ingredients to the site of action. Because the liposomal membrane is structurally similar to biological membranes, when liposomes are applied to a tissue, the liposomes start to merge with the cellular membranes and as the merging of the liposome and cell progresses, the liposomal contents are emptied into the cell where the active agent may act.

Liposomal formulations have been the focus of extensive investigation as the mode of delivery for many drugs. There is growing evidence that for topical administration, liposomes present several advantages over other formulations. Such advantages include reduced side-effects related to high systemic absorption of the administered drug, increased accumulation of the administered drug at the desired target, and the ability to administer a wide variety of drugs, both hydrophilic and hydrophobic, into the skin.

Several reports have detailed the ability of liposomes to deliver agents including high-molecular weight DNA into the skin. Compounds including analgesics, antibodies, hormones and high-molecular weight DNAs have been administered to the skin. The majority of applications resulted in the targeting of the upper epidermis.

Liposomes fall into two broad classes. Cationic liposomes are positively charged liposomes which interact with the negatively charged DNA molecules to form a stable complex. The positively charged DNA/liposome complex binds to the negatively charged cell surface and is internalized in an endosome. Due to the acidic pH within the endosome, the liposomes are ruptured, releasing their contents into the cell cytoplasm (Wang et al., *Biochem. Biophys. Res. Commun.*, 1987, 147, 980–985).

Liposomes which are pH-sensitive or negatively-charged, entrap DNA rather than complex with it. Since both the DNA and the lipid are similarly charged, repulsion rather than complex formation occurs. Nevertheless, some DNA is entrapped within the aqueous interior of these liposomes. pH-sensitive liposomes have been used to deliver DNA encoding the thymidine kinase gene to cell monolayers in culture. Expression of the exogenous gene was detected in the target cells (Zhou et al., *Journal of Controlled Release*, 1992, 19, 269–274).

One major type of liposomal composition includes phospholipids other than naturally-derived phosphatidylcholine. Neutral liposome compositions, for example, can be formed from dimyristoyl phosphatidylcholine (DMPC) or dipalmitoyl phosphatidylcholine (DPPC). Anionic liposome compositions generally are formed from dimyristoyl phosphatidylglycerol, while anionic fusogenic liposomes are formed primarily from dioleoyl phosphatidylethanolamine (DOPE). Another type of liposomal composition is formed from phosphatidylcholine (PC) such as, for example, soybean PC, and egg PC. Another type is formed from mixtures of phospholipid and/or phosphatidylcholine and/or cholesterol.

Several studies have assessed the topical delivery of liposomal drug formulations to the skin. Application of liposomes containing interferon to guinea pig skin resulted in a reduction of skin herpes sores while delivery of interferon via other means (e.g. as a solution or as an emulsion) were ineffective (Weiner et al., *Journal of Drug Targeting*, 1992, 2, 405–410). Further, an additional study tested the efficacy of interferon administered as part of a liposomal formulation to the administration of interferon using an aqueous system, and concluded that the liposomal formulation was superior to aqueous administration (du Plessis et al., *Antiviral Research*, 1992, 18, 259–265).

Non-ionic liposomal systems have also been examined to determine their utility in the delivery of drugs to the skin, in particular systems comprising non-ionic surfactant and cholesterol. Non-ionic liposomal formulations comprising Novasome™ I (glyceryl dilaurate/cholesterol/polyoxyethylene-10-stearyl ether) and Novasome™ II (glyceryl distearate/cholesterol/polyoxyethylene-10-stearyl ether) were used to deliver cyclosporin-A into the dermis of mouse skin. Results indicated that such non-ionic liposomal systems were effective in facilitating the deposition of cyclosporin-A into different layers of the skin (Hu et al. *S.T.P. Pharma. Sci.*, 1994, 4, 6, 466).

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters*, 1987, 223, 42; Wu et al., *Cancer Research*, 1993, 53, 3765).

Various liposomes comprising one or more glycolipids are known in the art. Papahadjopoulos et al. (*Ann. N.Y. Acad. Sci.*, 1987, 507, 64) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.A.*, 1988, 85, 6949). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Many liposomes comprising lipids derivatized with one or more hydrophilic polymers, and methods of preparation thereof, are known in the art. Sunamoto et al. (*Bull. Chem. Soc. Jpn.*, 1980, 53, 2778) described liposomes comprising a nonionic detergent, $2C_{12}15G$, that contains a PEG moiety. Illum et al. (*FEBS Lett.*, 1984, 167, 79) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Lett.*, 1990, 268, 235) described experiments demonstrating that liposomes comprising phosphatidylethanolamine (PE) derivatized with PEG or PEG stearate have significant increases in blood circulation half-lives. Blume et al. (*Biochimica et Biophysica Acta*, 1990, 1029, 91) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. EP 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

A limited number of liposomes comprising nucleic acids are known in the art. WO 96/40062 to Thierry et al. discloses methods for encapsulating high molecular weight nucleic acids in liposomes. U.S. Pat. No. 5,264,221 to Tagawa et al. discloses protein-bonded liposomes and asserts that the contents of such liposomes may include an antisense RNA. U.S. Pat. No. 5,665,710 to Rahman et al. describes certain methods of encapsulating oligodeoxynucleotides in liposomes. WO 97/04787 to Love et al. discloses liposomes comprising antisense oligonucleotides targeted to the raf gene.

Transfersomes are yet another type of liposomes, and are highly deformable lipid aggregates which are attractive candidates for drug delivery vehicles. Transfersomes may be described as lipid droplets which are so highly deformable that they are easily able to penetrate through pores which are smaller than the droplet. Transfersomes are adaptable to the environment in which they are used, e.g. they are self-optimizing (adaptive to the shape of pores in the skin), self-repairing, frequently reach their targets without fragmenting, and often self-loading. To make transfersomes it is possible to add surface edge-activators, usually surfactants, to a standard liposomal composition. Transfersomes have been used to deliver serum albumin to the skin. The transfersome-mediated delivery of serum albumin has been shown to be as effective as subcutaneous injection of a solution containing serum albumin.

Surfactants find wide application in formulations such as emulsions (including microemulsions) and liposomes. The most common way of classifying and ranking the properties of the many different types of surfactants, both natural and synthetic, is by the use of the hydrophile/lipophile balance (HLB). The nature of the hydrophilic group (also known as the "head") provides the most useful means for categorizing the different surfactants used in formulations (Rieger, in *Pharmaceutical Dosage Forms*, Marcel Dekker, Inc., New York, N.Y., 1988, p. 285).

If the surfactant molecule is not ionized, it is classified as a nonionic surfactant. Nonionic surfactants find wide application in pharmaceutical and cosmetic products and are usable over a wide range of pH values. In general their HLB values range from 2 to about 18 depending on their structure. Nonionic surfactants include nonionic esters such as ethylene glycol esters, propylene glycol esters, glyceryl esters, polyglyceryl esters, sorbitan esters, sucrose esters, and ethoxylated esters. Nonionic alkanolamides and ethers such as fatty alcohol ethoxylates, propoxylated alcohols, and ethoxylated/propoxylated block polymers are also included in this class. The polyoxyethylene surfactants are the most popular members of the nonionic surfactant class.

If the surfactant molecule carries a negative charge when it is dissolved or dispersed in water, the surfactant is classified as anionic. Anionic surfactants include carboxylates such as soaps, acyl lactylates, acyl amides of amino acids, esters of sulfuric acid such as alkyl sulfates and ethoxylated alkyl sulfates, sulfonates such as alkyl benzene sulfonates, acyl isethionates, acyl taurates and sulfosuccinates, and phosphates. The most important members of the anionic surfactant class are the alkyl sulfates and the soaps.

If the surfactant molecule carries a positive charge when it is dissolved or dispersed in water, the surfactant is classified as cationic. Cationic surfactants include quaternary ammonium salts and ethoxylated amines. The quaternary ammonium salts are the most used members of this class.

If the surfactant molecule has the ability to carry either a positive or negative charge, the surfactant is classified as amphoteric. Amphoteric surfactants include acrylic acid derivatives, substituted alkylamides, N-alkylbetaines and phosphatides.

The use of surfactants in drug products, formulations and in emulsions has been reviewed (Rieger, in *Pharmaceutical Dosage Forms*, Marcel Dekker, Inc., New York, N.Y., 1988, p. 285).

Penetration Enhancers

In one embodiment, the present invention employs various penetration enhancers to effect the efficient delivery of nucleic acids, particularly oligonucleotides, to the skin of animals. Most drugs are present in solution in both ionized and nonionized forms. However, usually only lipid soluble or lipophilic drugs readily cross cell membranes. It has been discovered that even non-lipophilic drugs may cross cell membranes if the membrane to be crossed is treated with a penetration enhancer. In addition to aiding the diffusion of non-lipophilic drugs across cell membranes, penetration enhancers also enhance the permeability of lipophilic drugs.

Penetration enhancers may be classified as belonging to one of five broad categories, i.e., surfactants, fatty acids, bile salts, chelating agents, and non-chelating non-surfactants (Lee et al., *Critical Reviews in Therapeutic Drug Carrier Systems*, 1991, p.92). Each of the above mentioned classes of penetration enhancers are described below in greater detail.

Surfactants: In connection with the present invention, surfactants (or "surface-active agents") are chemical entities which, when dissolved in an aqueous solution, reduce the surface tension of the solution or the interfacial tension between the aqueous solution and another liquid, with the result that absorption of oligonucleotides through the mucosa is enhanced. In addition to bile salts and fatty acids, these penetration enhancers include, for example, sodium lauryl sulfate, polyoxyethylene-9-lauryl ether and polyoxyethylene-20-cetyl ether) (Lee et al., *Critical Reviews in Therapeutic Drug Carrier Systems,* 1991, p.92); and perfluorochemical emulsions, such as FC-43. Takahashi et al., *J. Pharm. Pharmacol.*, 1988, 40, 252).

Fatty acids: Various fatty acids and their derivatives which act as penetration enhancers include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glycerol 1-monocaprate, 1-dodecylazacycloheptan-2-one, acylcarnitines, acylcholines, $C_{1-10}$ alkyl esters thereof (e.g., methyl, isopropyl and t-butyl), and mono- and di-glycerides thereof (i.e., oleate, laurate, caprate, myristate, palmitate, stearate, linoleate, etc.) (Lee et al., *Critical Reviews in Therapeutic Drug Carrier Systems*, 1991, p.92; Muranishi, *Critical Reviews in Therapeutic Drug Carrier Systems*, 1990, 7, 1–33; El Hariri et al., *J. Pharm. Pharmacol.*, 1992, 44, 651–654).

Bile salts: The physiological role of bile includes the facilitation of dispersion and absorption of lipids and fat-soluble vitamins (Brunton, Chapter 38 in: Goodman & Gilman's *The Pharmacological Basis of Therapeutics*, 9th Ed., Hardman et al. Eds., McGraw-Hill, New York, 1996, pp. 934–935). Various natural bile salts, and their synthetic derivatives, act as penetration enhancers. Thus the term "bile salts" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (sodium chenodeoxycholate), ursodeoxycholic acid (UDCA), sodium tauro-24,25-dihydro-fusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782–783; Muranishi, *Critical Reviews in Therapeutic Drug Carrier Systems*, 1990, 7, 1–33; Yamamoto et al., *J. Pharm. Exp. Ther.*, 1992, 263, 25; Yamashita et al., *J. Pharm. Sci.*, 1990, 79, 579–583).

Chelating Agents: Chelating agents, as used in connection with the present invention, can be defined as compounds that remove metallic ions from solution by forming complexes therewith, with the result that absorption of oligonucleotides through the mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, *J. Chromatogr.*, 1993, 618, 315–339). Chelating agents of the invention include but are not limited to disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) (Lee et al., *Critical Reviews in Therapeutic Drug Carrier Systems*, 1991, page 92; Muranishi, *Critical Reviews in Therapeutic Drug Carrier Systems*, 1990, 7, 1–33; Buur et al., *J. Control Rel.*, 1990, 14, 43–51).

Non-chelating non-surfactants: As used herein, non-chelating non-surfactant penetration enhancing compounds can be defined as compounds that demonstrate insignificant activity as chelating agents or as surfactants but that nonetheless enhance absorption of oligonucleotides through the alimentary mucosa (Muranishi, *Critical Reviews in Therapeutic Drug Carrier Systems*, 1990, 7, 1–33). This class of penetration enhancers include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621–626).

Agents that enhance uptake of oligonucleotides at the cellular level may also be added to the pharmaceutical and other compositions of the present invention. For example, cationic lipids, such as lipofectin (Junichi et al, U.S. Pat. No. 5,705,188), cationic glycerol derivatives, and polycationic molecules, such as polylysine (Lollo et al., PCT Application WO 97/30731), are also known to enhance the cellular uptake of oligonucleotides.

Other agents may be utilized to enhance the penetration of the administered nucleic acids, including glycols such as ethylene glycol and propylene glycol, pyrrols such as 2-pyrrol, azones, and terpenes such as limonene and menthone.

Carriers

Certain compositions of the present invention also incorporate carrier compounds in the formulation. As used herein, "carrier compound" or "carrier" can refer to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., *Antisense Res. Dev.*, 1995, 5, 115–121; Takakura et al., *Antisense & Nucl. Acid Drug Dev.*, 1996, 6, 177–183).

Excipients

In contrast to a carrier compound, a "pharmaceutical carrier" or "excipient" is a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, etc.); and wetting agents (e.g., sodium lauryl sulphate, etc.).

Pharmaceutically acceptable organic or inorganic excipient suitable for non-parenteral administration which do not deleteriously react with nucleic acids can also be used to formulate the compositions of the present invention. Suitable pharmaceutically acceptable carriers include, but are not limited to, water, salt solutions, alcohols, polyethylene glycols, gelatin, lactose, amylose, magnesium stearate, talc, silicic acid, viscous paraffin, hydroxymethylcellulose, polyvinylpyrrolidone and the like.

Formulations for topical administration of nucleic acids may include sterile and non-sterile aqueous solutions, non-aqueous solutions in common solvents such as alcohols, or solutions of the nucleic acids in liquid or solid oil bases. The solutions may also contain buffers, diluents and other suitable additives. Pharmaceutically acceptable organic or inorganic excipients suitable for non-parenteral administration which do not deleteriously react with nucleic acids can be used.

Suitable pharmaceutically acceptable excipients include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like.

Other Components

The compositions of the present invention may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the compositions of the present invention, such as dyes, flavoring agents, preservatives, antioxidants, opacifiers, thickening agents and stabilizers. However, such materials, when added, should not unduly interfere with the biological activities of the components of the compositions of the present invention. The formulations can be sterilized and, if desired, mixed with auxiliary agents, e.g., lubricants, preservatives, stabilizers, wetting agents, emulsifiers, salts for influencing osmotic pressure, buffers, colorings, flavorings and/or aromatic substances and the like which do not deleteriously interact with the nucleic acid(s) of the formulation.

Aqueous suspensions may contain substances which increase the viscosity of the suspension including, for example, sodium carboxymethylcellulose, sorbitol and/or dextran. The suspension may also contain stabilizers.

Certain embodiments of the invention provide pharmaceutical compositions containing (a) one or more antisense compounds and (b) one or more other chemotherapeutic agents which function by a non-antisense mechanism. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). See, generally, *The Merck Manual of Diagnosis and Therapy*, 15th Ed. 1987, pp. 1206–1228, Berkow et al., eds., Rahway, N.J. When used with the compounds of the invention, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to non-steroidal anti-inflammatory drugs and corticosteroids, and antiviral drugs, including but not limited to ribivirin, vidarabine, acyclovir and ganciclovir, may also be combined in compositions of the invention. See, generally, *The Merck Manual of Diagnosis and Therapy*, 15th Ed., Berkow et al., eds., 1987, Rahway, N.J., pages 2499–2506 and 46–49, respectively). Other non-antisense chemotherapeutic agents are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Numerous examples of antisense compounds are known in the art. Two or more combined compounds may be used together or sequentially.

The formulation of therapeutic compositions and their subsequent administration is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}$s found to be effective in in vitro and in vivo animal models. In general, dosage is from 0.01 ug to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.01 ug to 100 g per kg of body weight, once or more daily, to once every 20 years.

While the present invention has been described with specificity in accordance with certain of its preferred embodiments, the following examples serve only to illustrate the invention and are not intended to limit the same.

EXAMPLES

Example 1

Nucleoside Phosphoramidites for Oligonucleotide Synthesis Deoxy and 2'-alkoxy Amidites 2'-Deoxy and 2'-methoxy beta-cyanoethyldiisopropyl phosphoramidites were purchased from commercial sources (e.g. Chemgenes, Needham Mass. or Glen Research, Inc. Sterling Va.). Other 2'-O-alkoxy substituted nucleoside amidites were prepared as described in U.S. Pat. No. 5,506, 351, herein incorporated by reference. For oligonucleotides synthesized using 2'-alkoxy amidites, optimized synthesis cycles were developed that incorporate multiple steps coupling longer wait times relative to standard synthesis cycles.

The following abbreviations are used in the text: thin layer chromatography (TLC), melting point (MP), high pressure liquid chromatography (HPLC), Nuclear Magnetic Resonance (NMR), argon (Ar), methanol (MeOH), dichloromethane ($CH_2Cl_2$), triethylamine (TEA), dimethyl formamide (DMF), ethyl acetate (EtOAc), dimethyl sulfoxide (DMSO), tetrahydrofuran (THF).

Oligonucleotides containing 5-methyl-2'-deoxycytidine (5-Me-dC) nucleotides were synthesized according to published methods (Sanghvi, et. al., *Nucleic Acids Research*, 1993, 21, 3197–3203) using commercially available phosphoramidites (Glen Research, Sterling Va. or ChemGenes, Needham Mass.) or prepared as follows:

Preparation of 5'-O-Dimethoxytrityl-thymidine Intermediate for 5-methyl dC Amidite To a 50 L glass reactor equipped with air stirrer and Ar gas line was added thymidine (1.00 kg, 4.13 mol) in anhydrous pyridine (6 L) at ambient temperature. Dimethoxytrityl (DMT) chloride (1.47 kg, 4.34 mol, 1.05 eq) was added as a solid in four portions over 1 h. After 30 min, TLC indicated approx. 95% product, 2% thymidine, 5% DMT reagent and by-products and 2% 3',5'-bis DMT product ($R_f$ in EtOAc 0.45, 0.05, 0.98, 0.95 respectively). Saturated sodium bicarbonate (4 L) and $CH_2Cl_2$ were added with stirring (pH of the aqueous layer 7.5). An additional 18 L of water was added, the mixture was stirred, the phases were separated, and the organic layer was transferred to a second 50 L vessel. The aqueous layer was extracted with additional $CH_2Cl_2$ (2×2 L). The combined organic layer was washed with water (10 L) and then concentrated in a rotary evaporator to approx. 3.6 kg total weight. This was redissolved in $CH_2Cl_2$ (3.5 L), added to the reactor followed by water (6 L) and hexanes (13 L). The mixture was vigorously stirred and seeded to give a fine white suspended solid starting at the interface. After stirring for 1 h, the suspension was removed by suction through a ½" diameter teflon tube into a 20 L suction flask, poured onto a 25 cm Coors Buchner funnel, washed with water (2×3 L) and a mixture of hexanes-$CH_2Cl_2$ (4:1, 2×3 L) and allowed to air dry overnight in pans (1" deep). This was further dried in a vacuum oven (75° C., 0.1 mm Hg, 48 h) to a constant weight of 2072 g (93%) of a white solid, (mp 122–124° C.). TLC indicated a trace contamination of the bis DMT product. NMR spectroscopy also indicated that 1–2 mole percent pyridine and about 5 mole percent of hexanes was still present.

Preparation of 5'-O-Dimethoxytrityl-2'-deoxy-5-methylcytidine Intermediate for 5-methyl-dC Amidite To a 50 L Schott glass-lined steel reactor equipped with an electric stirrer, reagent addition pump (connected to an addition funnel), heating/cooling system, internal thermometer and an Ar gas line was added 5'-O-dimethoxytrityl-thymidine (3.00 kg, 5.51 mol), anhydrous acetonitrile (25 L) and TEA (12.3 L, 88.4 mol, 16 eq). The mixture was chilled with stirring to −10° C. internal temperature (external −20° C.). Trimethylsilylchloride (2.1 L, 16.5 mol, 3.0 eq) was added over 30 minutes while maintaining the internal temperature below −5° C., followed by a wash of anhydrous acetonitrile (1 L). Note: the reaction is mildly exothermic and copious hydrochloric acid fumes form over the course of the addition. The reaction was allowed to warm to 0° C. and the reaction progress was confirmed by TLC (EtOAc-hexanes 4:1; $R_f$ 0.43 to 0.84 of starting material and silyl product, respectively). Upon completion, triazole (3.05 kg, 44 mol, 8.0 eq) was added the reaction was cooled to −20° C. internal temperature (external −30° C.). Phosphorous oxychloride (1035 mL, 11.1 mol, 2.01 eq) was added over 60 min so as to maintain the temperature between −20° C. and −10° C. during the strongly exothermic process, followed by a wash of anhydrous acetonitrile (1 L). The reaction was warmed to 0° C. and stirred for 1 h. TLC indicated a complete conversion to the triazole product ($R_f$ 0.83 to 0.34 with the product spot glowing in long wavelength UV light). The reaction mixture was a peach-colored thick suspension, which turned darker red upon warming without apparent decomposition. The reaction was cooled to −15° C. internal temperature and water (5 L) was slowly added at a rate to maintain the temperature below +10° C. in order to quench the reaction and to form a homogenous solution. (Caution: this reaction is initially very strongly exothermic). Approximately one-half of the reaction volume (22 L) was transferred by air pump to another vessel, diluted with EtOAc (12 L) and extracted with water (2×8 L). The combined water layers were back-extracted with EtOAc (6 L). The water layer was discarded and the organic layers were concentrated in a 20 L rotary evaporator to an oily foam. The foam was coevaporated with anhydrous acetonitrile (4 L) to remove EtOAc. (note: dioxane may be used instead of anhydrous acetonitrile if dried to a hard foam). The second half of the reaction was treated in the same way. Each residue was dissolved in dioxane (3 L) and concentrated ammonium hydroxide (750 mL) was added. A homogenous solution formed in a few minutes and the reaction was allowed to stand overnight (although the reaction is complete within 1 h).

TLC indicated a complete reaction (product $R_f$ 0.35 in EtOAc-MeOH 4:1). The reaction solution was concentrated on a rotary evaporator to a dense foam. Each foam was slowly redissolved in warm EtOAc (4 L; 50° C.), combined in a 50 L glass reactor vessel, and extracted with water (2×4L) to remove the triazole by-product. The water was back-extracted with EtOAc (2 L). The organic layers were combined and concentrated to about 8 kg total weight, cooled to 0° C. and seeded with crystalline product. After 24 hours, the first crop was collected on a 25 cm Coors Buchner funnel and washed repeatedly with EtOAc (3×3L) until a white powder was left and then washed with ethyl ether (2×3L). The solid was put in pans (1" deep) and allowed to air dry overnight. The filtrate was concentrated to an oil, then redissolved in EtOAc (2 L), cooled and seeded as before. The second crop was collected and washed as before (with proportional solvents) and the filtrate was first extracted with water (2×1L) and then concentrated to an oil. The residue was dissolved in EtOAc (1 L) and yielded a third crop which was treated as above except that more washing was required to remove a yellow oily layer.

After air-drying, the three crops were dried in a vacuum oven (50° C., 0.1 mm Hg, 24 h) to a constant weight (1750, 600 and 200 g, respectively) and combined to afford 2550 g (85%) of a white crystalline product (MP 215–217° C.) when TLC and NMR spectroscopy indicated purity. The mother liquor still contained mostly product (as determined by TLC) and a small amount of triazole (as determined by NMR spectroscopy), bis DMT product and unidentified minor impurities. If desired, the mother liquor can be purified by silica gel chromatography using a gradient of MeOH (0–25%) in EtOAc to further increase the yield.

Preparation of 5'-O-Dimethoxytrityl-2'-deoxy-N-4-benzoyl-5-methylcytidine Penultimate Intermediate for 5-methyl dC Amidite Crystalline 5'-O-dimethoxytrityl-5-methyl-2'-deoxycytidine (2000 g, 3.68 mol) was dissolved in anhydrous DMF (6.0 kg) at ambient temperature in a 50 L glass reactor vessel equipped with an air stirrer and argon line. Benzoic anhydride (Chem Impex not Aldrich, 874 g, 3.86 mol, 1.05 eq) was added and the reaction was stirred at ambient temperature for 8 h. TLC (CH$_2$Cl$_2$-EtOAc; CH$_2$Cl$_2$-EtOAc 4:1; $R_f$ 0.25) indicated approx. 92% complete reaction. An additional amount of benzoic anhydride (44 g, 0.19 mol) was added. After a total of 18 h, TLC indicated approx. 96% reaction completion. The solution was diluted with EtOAc (20 L), TEA (1020 mL, 7.36 mol, ca 2.0 eq) was added with stirring, and the mixture was extracted with water (15 L, then 2×10 L). The aqueous layer was removed (no back-extraction was needed) and the organic layer was concentrated in 2×20 L rotary evaporator flasks until a foam began to form. The residues were coevaporated with acetonitrile (1.5 L each) and dried (0.1 mm Hg, 25° C., 24 h) to 2520 g of a dense foam. High pressure liquid chromatography (HPLC) revealed a contamination of 6.3% of N4, 3'-O-dibenzoyl product, but very little other impurities.

THe product was purified by Biotage column chromatography (5 kg Biotage) prepared with 65:35:1 hexanes-EtOAc-TEA (4L). The crude product (800 g),dissolved in CH$_2$Cl$_2$ (2 L), was applied to the column. The column was washed with the 65:35:1 solvent mixture (20 kg), then 20:80:1 solvent mixture (10 kg), then 99:1 EtOAc:TEA (17 kg). The fractions containing the product were collected, and any fractions containing the product and impurities were retained to be resubjected to column chromatography. The column was re-equilibrated with the original 65:35:1 solvent mixture (17 kg). A second batch of crude product (840 g) was applied to the column as before. The column was washed with the following solvent gradients: 65:35:1 (9 kg), 55:45:1 (20 kg), 20:80:1 (10 kg), and 99:1 EtOAc:TEA (15 kg). The column was reequilibrated as above, and a third batch of the crude product (850 g) plus impure fractions recycled from the two previous columns (28 g) was purified following the procedure for the second batch. The fractions containing pure product combined and concentrated on a 20L rotary evaporator, co-evaporated with acetontirile (3 L) and dried (0.1 mm Hg, 48 h, 25° C.) to a constant weight of 2023 g (85%) of white foam and 20 g of slightly contaminated product from the third run. HPLC indicated a purity of 99.8% with the balance as the diBenzoyl product.

[5'-O-(4,4'-Dimethoxytriphenylmethyl)-2'-deoxy-N$^4$-benzoyl-5-methylcytidin-3'-O-yl]-2-cyanoethyl-N,N-diisopropylphosphoramidite (5-methyl dC Amidite)

5'-O-(4,4'-Dimethoxytriphenylmethyl)-2'-deoxy-N$^4$-benzoyl-5-methylcytidine (998 g, 1.5 mol) was dissolved in anhydrous DMF (2 L). The solution was co-evaporated with toluene (300 ml) at 50° C. under reduced pressure, then cooled to room temperature and 2-cyanoethyl tetraisopropylphosphorodiamidite (680 g, 2.26 mol) and tetrazole (52.5 g, 0.75 mol) were added. The mixture was shaken until all tetrazole was dissolved, N-methylimidazole (15 ml) was added and the mixture was left at room temperature for 5 hours. TEA (300 ml) was added, the mixture was diluted with DMF (2.5 L) and water (600 ml), and extracted with hexane (3×3 L). The mixture was diluted with water (1.2 L) and extracted with a mixture of toluene (7.5 L) and hexane (6 L). The two layers were separated, the upper layer was washed with DMF-water (7:3 v/v, 3×2 L) and water (3×2 L), and the phases were separated. The organic layer was dried (Na$_2$SO$_4$), filtered and rotary evaporated. The residue was co-evaporated with acetonitrile (2×2 L) under reduced pressure and dried to a constant weight (25° C., 0.1 mm Hg, 40 h) to afford 1250 g an off-white foam solid (96%).

2'-Fluoro Amidites

2'-Fluorodeoxyadenosine Amidites

2'-fluoro oligonucleotides were synthesized as described previously [Kawasaki, et. al., *J. Med. Chem.*, 1993, 36, 831–841] and U.S. Pat. No. 5,670,633, herein incorporated by reference. The preparation of 2'-fluoropyrimidines containing a 5-methyl substitution are described in U.S. Pat. No. 5,861,493. Briefly, the protected nucleoside N6-benzoyl-2'-deoxy-2'-fluoroadenosine was synthesized utilizing commercially available 9-beta-D-arabinofuranosyladenine as starting material and whereby the 2'-alpha-fluoro atom is introduced by a S$_N$2-displacement of a 2'-beta-triflate group. Thus N6-benzoyl-9-beta-D-arabinofuranosyladenine was selectively protected in moderate yield as the 3',5'-ditetrahydropyranyl (THP) intermediate. Deprotection of the THP and N6-benzoyl groups was accomplished using standard methodologies to obtain the 5'-dimethoxytrityl-(DMT) and 5'-DMT-3'-phosphoramidite intermediates.

2'-Fluorodeoxyguanosine

The synthesis of 2'-deoxy-2'-fluoroguanosine was accomplished using tetraisopropyldisiloxanyl (TPDS) protected 9-beta-D-arabinofuranosylguanine as starting material, and conversion to the intermediate isobutyryl-arabinofuranosylguanosine. Alternatively, isobutyryl-arabinofuranosylguanosine was prepared as described by Ross et al., (Nucleosides & Nucleosides, 16, 1645, 1997). Deprotection of the TPDS group was followed by protection of the hydroxyl group with THP to give isobutyryl di-THP protected arabinofuranosylguanine. Selective O-deacylation and triflation was followed by treatment of the crude product with fluoride, then deprotection of the THP groups. Standard methodologies were used to obtain the 5'-DMT- and 5'-DMT-3'-phosphoramidites.

2'-Fluorouridine

Synthesis of 2'-deoxy-2'-fluorouridine was accomplished by the modification of a literature procedure in which 2,2'-anhydro-1-beta-D-arabinofuranosyluracil was treated with 70% hydrogen fluoride-pyridine. Standard procedures were used to obtain the 5'-DMT and 5'-DMT-3'phosphoramidites.

2'-Fluorodeoxycytidine

2'-deoxy-2'-fluorocytidine was synthesized via amination of 2'-deoxy-2'-fluorouridine, followed by selective protection to give N4-benzoyl-2'-deoxy-2'-fluorocytidine. Standard procedures were used to obtain the 5'-DMT and 5'-DMT-3'phosphoramidites.

2'-O-(2-Methoxyethyl) Modified Amidites

2'-O-Methoxyethyl-substituted nucleoside amidites (otherwise known as MOE amidites) are prepared as follows, or alternatively, as per the methods of Martin, P., (Helvetica Chimica Acta, 1995, 78, 486–504).

Preparation of 2'-O-(2-methoxyethyl)-5-methyluridine Intermediate 2,2'-Anhydro-5-methyl-uridine (2000 g, 8.32 mol), tris(2-methoxyethyl)borate (2504 g, 10.60 mol), sodium bicarbonate (60 g, 0.70 mol) and anhydrous 2-methoxyethanol (5 L) were combined in a 12 L three necked flask and heated to 130° C. (internal temp) at atmospheric pressure, under an argon atmosphere with stirring for 21 h. TLC indicated a complete reaction. The solvent was removed under reduced pressure until a sticky gum formed (50–85° C. bath temp and 100–11 mm Hg) and the residue was redissolved in water (3 L) and heated to boiling for 30 min in order the hydrolyze the borate esters. The water was removed under reduced pressure until a foam began to form and then the process was repeated. HPLC indicated about 77% product, 15% dimer (5' of product attached to 2' of starting material) and unknown derivatives, and the balance was a single unresolved early eluting peak.

The gum was redissolved in brine (3 L), and the flask was rinsed with additional brine (3 L). The combined aqueous solutions were extracted with chloroform (20 L) in a heavier-than continuous extractor for 70 h. The chloroform layer was concentrated by rotary evaporation in a 20 L flask to a sticky foam (2400 g). This was coevaporated with MeOH (400 mL) and EtOAc (8 L) at 75° C. and 0.65 atm until the foam dissolved at which point the vacuum was lowered to about 0.5 atm. After 2.5 L of distillate was collected a precipitate began to form and the flask was removed from the rotary evaporator and stirred until the suspension reached ambient temperature. EtOAc (2 L) was added and the slurry was filtered on a 25 cm table top Buchner funnel and the product was washed with EtOAc (3×2 L). The bright white solid was air dried in pans for 24 h then further dried in a vacuum oven (50° C., 0.1 mm Hg, 24 h) to afford 1649 g of a white crystalline solid (mp 115.5–116.5° C.).

The brine layer in the 20 L continuous extractor was further extracted for 72 h with recycled chloroform. The chloroform was concentrated to 120 g of oil and this was combined with the mother liquor from the above filtration (225 g), dissolved in brine (250 mL) and extracted once with chloroform (250 mL). The brine solution was continuously extracted and the product was crystallized as described above to afford an additional 178 g of crystalline product containing about 2% of thymine. The combined yield was 1827 g (69.4%). HPLC indicated about 99.5% purity with the balance being the dimer.

Preparation of 5'-O-DMT-2'-O-(2-methoxyethyl)-5-methyluridine Penultimate Intermediate In a 50 L glass-lined steel reactor, 2'-O-(2-methoxyethyl)-5-methyl-uridine (MOE-T, 1500 g, 4.738 mol), lutidine (1015 g, 9.476 mol) were dissolved in anhydrous acetonitrile (15 L). The solution was stirred rapidly and chilled to −10° C. (internal temperature). Dimethoxytriphenylmethyl chloride (1765.7 g, 5.21 mol) was added as a solid in one portion. The reaction was allowed to warm to −2° C. over 1 h. (Note: The reaction was monitored closely by TLC (EtOAc) to determine when to stop the reaction so as to not generate the undesired bis-DMT substituted side product). The reaction was allowed to warm from −2 to 3° C. over 25 min. then quenched by adding MeOH (300 mL) followed after 10 min by toluene (16 L) and water (16 L). The solution was transferred to a clear 50 L vessel with a bottom outlet, vigorously stirred for 1 minute, and the layers separated. The aqueous layer was removed and the organic layer was washed successively with 10% aqueous citric acid (8 L) and water (12 L). The product was then extracted into the aqueous phase by washing the toluene solution with aqueous sodium hydroxide (0.5N, 16 L and 8 L). The combined aqueous layer was overlayed with toluene (12 L) and solid citric acid (8 moles, 1270 g) was added with vigorous stirring to lower the pH of the aqueous layer to 5.5 and extract the product into the toluene. The organic layer was washed with water (10 L) and TLC of the organic layer indicated a trace of DMT-O-Me, bis DMT and dimer DMT.

The toluene solution was applied to a silica gel column (6 L sintered glass funnel containing approx. 2 kg of silica gel slurried with toluene (2 L) and TEA (25 mL)) and the fractions were eluted with toluene (12 L) and EtOAc (3×4 L) using vacuum applied to a filter flask placed below the column. The first EtOAc fraction containing both the desired product and impurities were resubjected to column chromatography as above. The clean fractions were combined, rotary evaporated to a foam, coevaporated with acetonitrile (6 L) and dried in a vacuum oven (0.1 mm Hg, 40 h, 40° C.) to afford 2850 g of a white crisp foam. NMR spectroscopy indicated a 0.25 mole % remainder of acetonitrile (calculates to be approx. 47 g) to give a true dry weight of 2803 g (96%). HPLC indicated that the product was 99.41% pure, with the remainder being 0.06 DMT-O-Me, 0.10 unknown, 0.44 bis DMT, and no detectable dimer DMT or 3'-O-DMT.

Preparation of [5'-O-(4,4'-Dimethoxytriphenylmethyl)-2'-O-(2-methoxyethyl)-5-methyluridin-3'-O-yl]-2-cyanoethyl-N,N'-diisopropylphosphoramidite (MOE T Amidite)

5'-O-(4,4'-Dimethoxytriphenylmethyl)-2'-O-(2-methoxyethyl)-5-methyluridine (1237 g, 2.0 mol) was dissolved in anhydrous DMF (2.5 L). The solution was co-evaporated with toluene (200 ml) at 50° C. under reduced pressure, then cooled to room temperature and 2-cyanoethyl tetraisopropylphosphorodiamidite (900 g, 3.0 mol) and tetrazole (70 g, 1.0 mol) were added. The mixture was shaken until all tetrazole was dissolved, N-methylimidazole (20 ml) was added and the solution was left at room temperature for 5 hours. TEA (300 ml) was added, the mixture was diluted with DMF (3.5 L) and water (600 ml) and extracted with hexane (3×3L). The mixture was diluted with water (1.6 L) and extracted with the mixture of toluene (12 L) and hexanes (9 L). The upper layer was washed with DMF-water (7:3 v/v, 3×3 L) and water (3×3 L). The organic layer was dried ($Na_2SO_4$), filtered and evaporated. The residue was co-evaporated with acetonitrile (2×2 L) under reduced pressure and dried in a vacuum oven (25° C., 0.1 mm Hg, 40 h) to afford 1526 g of an off-white foamy solid (95%).

Preparation of 5'-O-Dimethoxytrityl-2'-O-(2-methoxyethyl)-5-methylcytidine Intermediate To a 50 L Schott glass-lined steel reactor equipped with an electric stirrer, reagent addition pump (connected to an addition funnel), heating/cooling system, internal thermometer and argon gas line was added 5'-O-dimethoxytrityl-2'-O-(2-methoxyethyl)-5-methyl-uridine (2.616 kg, 4.23 mol, purified by base extraction only and no scrub column), anhydrous acetonitrile (20 L), and TEA (9.5 L, 67.7 mol, 16 eq). The mixture was chilled with stirring to −10° C. internal temperature (external −20° C.). Trimethylsilylchloride (1.60 L, 12.7 mol, 3.0 eq) was added over 30 min. while maintaining the internal temperature below −5° C., followed by a wash of anhydrous acetonitrile (1 L). (Note: the reaction is mildly exothermic and copious hydrochloric acid fumes form over the course of the addition). The reaction was allowed to warm to 0° C. and the reaction progress was confirmed by TLC (EtOAc, $R_f$ 0.68 and 0.87 for starting material and silyl product, respectively). Upon completion, triazole (2.34 kg, 33.8 mol, 8.0 eq) was added the reaction was cooled to −20° C. internal temperature (external −30° C.). Phosphorous oxychloride (793 mL, 8.51 mol, 2.01 eq) was added slowly over 60 min so as to maintain the temperature between −20° C. and −10° C. (note: strongly exothermic), followed by a wash of anhydrous acetonitrile (1 L). The reaction was warmed to 0° C. and stirred for 1 h, at which point it was an off-white thick suspension. TLC indicated a complete conversion to the triazole product (EtOAc, $R_f$ 0.87 to 0.75 with the product spot glowing in long wavelength UV light). The reaction was cooled to −15° C. and water (5 L) was slowly added at a rate to maintain the temperature below +10° C. in order to quench the reaction and to form a homogenous solution. (Caution: this reaction is initially very strongly exothermic). Approximately one-half of the reaction volume (22 L) was transferred by air pump to another vessel, diluted with EtOAc (12 L) and extracted with water (2×8 L). The second half of the reaction was treated in the same way. The combined aqueous layers were back-extracted with EtOAc (8 L) The organic layers were combined and concentrated in a 20 L rotary evaporator to an oily foam. The foam was coevaporated with anhydrous acetonitrile (4 L) to remove EtOAc. (note: dioxane may be used instead of anhydrous acetonitrile if dried to a hard foam). The residue was dissolved in dioxane (2 L) and concentrated ammonium hydroxide (750 mL) was added. A homogenous solution formed in a few minutes and the reaction was allowed to stand overnight.

TLC indicated a complete reaction ($CH_2Cl_2$-acetone-MeOH, 20:5:3, $R_f$ 0.51). The reaction solution was concentrated on a rotary evaporator to a dense foam and slowly redissolved in warm $CH_2Cl_2$ (4 L, 40° C.) and transferred to a 20 L glass extraction vessel equipped with a air-powered stirrer. The organic layer was extracted with water (2×6 L) to remove the triazole by-product. (Note: In the first extraction an emulsion formed which took about 2 h to resolve). The water layer was back-extracted with $CH_2Cl_2$ (2×2 L), which in turn was washed with water (3 L). The combined organic layer was concentrated in 2×20 L flasks to a gum and then recrystallized from EtOAc seeded with crystalline product. After sitting overnight, the first crop was collected on a 25 cm Coors Buchner funnel and washed repeatedly with EtOAc until a white free-flowing powder was left (about 3×3 L). The filtrate was concentrated to an oil recrystallized from EtOAc, and collected as above. The solid was air-dried in pans for 48 h, then further dried in a vacuum oven (50° C., 0.1 mm Hg, 17 h) to afford 2248 g of a bright white, dense solid (86%). An HPLC analysis indicated both crops to be 99.4% pure and NMR spectroscopy indicated only a faint trace of EtOAc remained.

Preparation of 5'-O-dimethoxytrityl-2'-O-(2-methoxyethyl)-N-4-benzoyl-5-methyl-cytidine Penultimate Intermediate:

Crystalline 5'-O-dimethoxytrityl-2'-O-(2-methoxyethyl)-5-methyl-cytidine (1000 g, 1.62 mol) was suspended in anhydrous DMF (3 kg) at ambient temperature and stirred under an Ar atmosphere. Benzoic anhydride (439.3 g, 1.94 mol) was added in one portion. The solution clarified after 5 hours and was stirred for 16 h. HPLC indicated 0.45% starting material remained (as well as 0.32% N4, 3'-O-bis Benzoyl). An additional amount of benzoic anhydride (6.0 g, 0.0265 mol) was added and after 17 h, HPLC indicated no starting material was present. TEA (450 mL, 3.24 mol) and toluene (6 L) were added with stirring for 1 minute. The solution was washed with water (4×4 L), and brine (2×4 L). The organic layer was partially evaporated on a 20 L rotary evaporator to remove 4 L of toluene and traces of water. HPLC indicated that the bis benzoyl side product was present as a 6% impurity. The residue was diluted with toluene (7 L) and anhydrous DMSO (200 mL, 2.82 mol) and sodium hydride (60% in oil, 70 g, 1.75 mol) was added in one portion with stirring at ambient temperature over 1 h. The reaction was quenched by slowly adding then washing with aqueous citric acid (10%, 100 mL over 10 min, then 2×4 L), followed by aqueous sodium bicarbonate (2%, 2 L), water (2×4 L) and brine (4 L). The organic layer was concentrated on a 20 L rotary evaporator to about 2 L total volume. The residue was purified by silica gel column chromatography (6 L Buchner funnel containing 1.5 kg of silica gel wetted with a solution of EtOAc-hexanes-TEA (70:29:1)). The product was eluted with the same solvent (30 L) followed by straight EtOAc (6 L). The fractions containing the product were combined, concentrated on a rotary evaporator to a foam and then dried in a vacuum oven (50° C., 0.2 mm Hg, 8 h) to afford 1155 g of a crisp, white foam (98%). HPLC indicated a purity of >99.7%.

Preparation of [5'-O-(4,4'-Dimethoxytriphenylmethyl)-2'-O-(2-methoxyethyl)-N$^4$-benzoyl-5-methylcytidin-3'-O-yl]-2-cyanoethyl-N, N-diisopropylphosphoramidite (MOE 5-Me-C Amidite)

5'-O— (4,4'-Dimethoxytriphenylmethyl)-2'-O—(2-methoxyethyl)-N$^4$-benzoyl-5-methylcytidine (1082 g, 1.5 mol) was dissolved in anhydrous DMF (2 L) and co-evaporated with toluene (300 ml) at 50° C. under reduced pressure. The mixture was cooled to room temperature and 2-cyanoethyl tetraisopropylphosphorodiamidite (680 g, 2.26 mol) and tetrazole (52.5 g, 0.75 mol) were added. The mixture was shaken until all tetrazole was dissolved, N-methylimidazole (30 ml) was added, and the mixture was left at room temperature for 5 hours. TEA (300 ml) was added, the mixture was diluted with DMF (1 L) and water (400 ml) and extracted with hexane (3×3 L). The mixture was diluted with water (1.2 L) and extracted with a mixture of toluene (9 L) and hexanes (6 L). The two layers were separated and the upper layer was washed with DMF-water (60:40 v/v, 3×3 L) and water (3×2 L). The organic layer was dried ($Na_2SO_4$), filtered and evaporated. The residue was co-evaporated with acetonitrile (2×2 L) under reduced pressure and dried in a vacuum oven (25° C., 0.1 mm Hg, 40 h) to afford 1336 g of an off-white foam (97%).

Preparation of [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A Amdite)

5'-O-(4,4'-Dimethoxytriphenylmethyl)-2'-O-(2-methoxyethyl)-$N^6$-benzoyladenosine (purchased from Reliable Biopharmaceutical, St. Lois, Mo.), 1098 g, 1.5 mol) was dissolved in anhydrous DMF (3 L) and co-evaporated with toluene (300 ml) at 50° C. The mixture was cooled to room temperature and 2-cyanoethyl tetraisopropylphosphorodiamidite (680 g, 2.26 mol) and tetrazole (78.8 g, 1.24 mol) were added. The mixture was shaken until all tetrazole was dissolved, N-methylimidazole (30 ml) was added, and mixture was left at room temperature for 5 hours. TEA (300 ml) was added, the mixture was diluted with DMF (1 L) and water (400 ml) and extracted with hexanes (3×3 L). The mixture was diluted with water (1.4 L) and extracted with the mixture of toluene (9 L) and hexanes (6 L). The two layers were separated and the upper layer was washed with DMF-water (60:40, v/v, 3×3 L) and water (3×2 L). The organic layer was dried ($Na_2SO_4$), filtered and evaporated to a sticky foam. The residue was co-evaporated with acetonitrile (2.5 L) under reduced pressure and dried in a vacuum oven (25° C., 0.1 mm Hg, 40 h) to afford 1350 g of an off-white foam solid (96%).

Prepartion of [5'-O-(4,4'-Dimethoxytriphenylmethyl)-2'-O-(2-methoxyethyl)-$N^4$-isobutyrylguanosin-3'-O-yl]-2-cyanoethyl-N, N-diisopropylphosphoramidite (MOE G Amidite)

5'-O-(4,4'-Dimethoxytriphenylmethyl)-2'-O-(2-methoxyethyl)-$N^4$-isobutyrlguanosine (purchased from Reliable Biopharmaceutical, St. Louis, Mo., 1426 g, 2.0 mol) was dissolved in anhydrous DMF (2 L). The solution was co-evaporated with toluene (200 ml) at 50° C., cooled to room temperature and 2-cyanoethyl tetraisopropylphosphorodiamidite (900 g, 3.0 mol) and tetrazole (68 g, 0.97 mol) were added. The mixture was shaken until all tetrazole was dissolved, N-methylimidazole (30 ml) was added, and the mixture was left at room temperature for 5 hours. TEA (300 ml) was added, the mixture was diluted with DMF (2 L) and water (600 ml) and extracted with hexanes (3×3 L). The mixture was diluted with water (2 L) and extracted with a mixture of toluene (10 L) and hexanes (5 L). The two layers were separated and the upper layer was washed with DMF-water (60:40, v/v, 3×3 L). EtOAc (4 L) was added and the solution was washed with water (3×4 L). The organic layer was dried ($Na_2SO_4$), filtered and evaporated to approx. 4 kg. Hexane (4 L) was added, the mixture was shaken for 10 min, and the supernatant liquid was decanted. The residue was co-evaporated with acetonitrile (2×2 L) under reduced pressure and dried in a vacuum oven (25° C., 0.1 mm Hg, 40 h) to afford 1660 g of an off-white foamy solid (91%).

2'-O-(Aminooxyethyl) Nucleoside Amidites and 2'-O-(dimethylaminooxyethyl) Nucleoside Amidites 2'-(Dimethylaminooxyethoxy) Nucleoside Amidites 2'-(Dimethylaminooxyethoxy) nucleoside amidites (also known in the art as 2'-O-(dimethylaminooxyethyl) nucleoside amidites) are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine.

5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC ($R_f$ 0.22, EtOAc) indicated a complete reaction. The solution was concentrated under reduced pressure to a thick oil. This was partitioned between $CH_2Cl_2$ (1 L) and saturated sodium bicarbonate (2×1 L) and brine (1 L). The organic layer was dried over sodium sulfate, filtered, and concentrated under reduced pressure to a thick oil. The oil was dissolved in a 1:1 mixture of EtOAc and ethyl ether (600 mL) and cooling the solution to −10° C. afforded a white crystalline solid which was collected by filtration, washed with ethyl ether (3×200 mL) and dried (40° C., 1 mm Hg, 24 h) to afford 149 g of white solid (74.8%). TLC and NMR spectroscopy were consistent with pure product.

5'-O-tert-Butyldiphenylsilyl-2'-O-(2-hydroxyethyl)-5-methyluridine

In the fume hood, ethylene glycol (350 mL, excess) was added cautiously with manual stirring to a 2 L stainless steel pressure reactor containing borane in tetrahydrofuran (1.0 M, 2.0 eq, 622 mL). (Caution: evolves hydrogen gas). 5'-O-tert-Butyldiphenylsilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure <100 psig). The reaction vessel was cooled to ambient temperature and opened. TLC (EtOAc, $R_f$ 0.67 for desired product and $R_f$ 0.82 for ara-T side product) indicated about 70% conversion to the product. The solution was concentrated under reduced pressure (10 to 1 mm Hg) in a warm water bath (40–100° C.) with the more extreme conditions used to remove the ethylene glycol. (Alternatively, once the THF has evaporated the solution can be diluted with water and the product extracted into EtOAc). The residue was purified by column chromatography (2 kg silica gel, EtOAc-hexanes gradient 1:1 to 4:1). The appropriate fractions were combined, evaporated and dried to afford 84 g of a white crisp foam (50%), contaminated starting material (17.4 g, 12% recovery) and pure reusable starting material (20 g, 13% recovery). TLC and NMR spectroscopy were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol) and dried over $P_2O_5$ under high vacuum for two days at 40° C. The reaction mixture was flushed with argon and dissolved in dry THF (369.8 mL, Aldrich, sure seal bottle). Diethyl-azodicarboxylate (6.98 mL, 44.36 mmol) was added dropwise to the reaction mixture with the rate of addition maintained such that the resulting deep red coloration is just discharged before adding the next drop. The reaction mixture was stirred for 4 hrs., after which time TLC (EtOAc:hexane, 60:40) indicated that the reaction was complete. The solvent was evaporated in vacuuo and the residue purified by flash column chromatography (eluted with 60:40 EtOAc:hexane), to yield 2'-O-([2-phthalimidoxy)ethyl]-5'-t-butyldiphenylsilyl-5-methyluridine as white foam (21.819 g, 86%) upon rotary evaporation.

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at $-10°$ C. to $0°$ C. After 1 h the mixture was filtered, the filtrate washed with ice cold $CH_2Cl_2$, and the combined organic phase was washed with water and brine and dried (anhydrous $Na_2SO_4$). The solution was filtered and evaporated to afford 2'-O-(aminooxyethyl) thymidine, which was then dissolved in MeOH (67.5 mL). Formaldehyde (20% aqueous solution, w/w, 1.1 eq.) was added and the resulting mixture was stirred for 1 h. The solvent was removed under vacuum and the residue was purified by column chromatography to yield 5'-O-tert-butyldiphenylsilyl-2'-O-[(2-formadoximinooxy) ethyl]-5-methyluridine as white foam (1.95 g, 78%) upon rotary evaporation.

5'-O-tert-Butyldiphenylsilyl-2'-O-[N,N dimethylaminooxyethyl]-5-methyluridine

5'-O-tert-butyldiphenylsilyl-2'-O-[(2-formadoximinooxy) ethyl]-5-methyluridine (1.77 g, 3.12 mmol) was dissolved in a solution of 1M pyridinium p-toluenesulfonate (PPTS) in dry MeOH (30.6 mL) and cooled to $10°$ C. under inert atmosphere. Sodium cyanoborohydride (0.39 g, 6.13 mmol) was added and the reaction mixture was stirred. After 10 minutes the reaction was warmed to room temperature and stirred for 2 h. while the progress of the reaction was monitored by TLC (5% MeOH in $CH_2Cl_2$). Aqueous $NaHCO_3$ solution (5%, 10 mL) was added and the product was extracted with EtOAc (2×20 mL). The organic phase was dried over anhydrous $Na_2SO_4$, filtered, and evaporated to dryness. This entire procedure was repeated with the resulting residue, with the exception that formaldehyde (20% w/w, 30 mL, 3.37 mol) was added upon dissolution of the residue in the PPTS/MeOH solution. After the extraction and evaporation, the residue was purified by flash column chromatography and (eluted with 5% MeOH in $CH_2Cl_2$) to afford 5'-O-tert-butyldiphenylsilyl-2'-O-[N,N-dimethylaminooxyethyl]-5-methyluridine as a white foam (14.6 g, 80%) upon rotary evaporation.

2'-O-(dimethylaminooxyethyl)-5-methyluridine

Triethylamine trihydrofluoride (3.91 mL, 24.0 mmol) was dissolved in dry THF and TEA (1.67 mL, 12 mmol, dry, stored over KOH) and added to 5'-O-tert-butyldiphenylsilyl-2'-O-[N,N-dimethylaminooxyethyl]-5-methyluridine (1.40 g, 2.4 mmol). The reaction was stirred at room temperature for 24 hrs and monitored by TLC (5% MeOH in $CH_2Cl_2$). The solvent was removed under vacuum and the residue purified by flash column chromatography (eluted with 10% MeOH in $CH_2Cl_2$) to afford 2'-O-(dimethylaminooxyethyl)-5-methyluridine (766 mg, 92.5%) upon rotary evaporation of the solvent.

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at $40°$ C., co-evaporated with anhydrous pyridine (20 mL), and dissolved in pyridine (11 mL) under argon atmosphere. 4-dimethylaminopyridine (26.5 mg, 2.60 mmol) and 4,4'-dimethoxytrityl chloride (880 mg, 2.60 mmol) were added to the pyridine solution and the reaction mixture was stirred at room temperature until all of the starting material had reacted. Pyridine was removed under vacuum and the residue was purified by column chromatography (eluted with 10% MeOH in $CH_2Cl_2$ containing a few drops of pyridine) to yield 5'-O-DMT-2'-O-(dimethylaminooxyethyl)-5-methyluridine (1.13 g, 80%) upon rotary evaporation.

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL), N,N-diisopropylamine tetrazonide (0.29 g, 1.67 mmol) was added and the mixture was dried over $P_2O_5$ under high vacuum overnight at $40°$ C. This was dissolved in anhydrous acetonitrile (8.4 mL) and 2-cyanoethyl-N,N,$N^1$,$N^1$-tetraisopropylphosphoramidite (2.12 mL, 6.08 mmol) was added. The reaction mixture was stirred at ambient temperature for 4 h under inert atmosphere. The progress of the reaction was monitored by TLC (hexane:EtOAc 1:1). The solvent was evaporated, then the residue was dissolved in EtOAc (70 mL) and washed with 5% aqueous $NaHCO_3$ (40 mL). The EtOAc layer was dried over anhydrous $Na_2SO_4$, filtered, and concentrated. The residue obtained was purified by column chromatography (EtOAc as eluent) to afford 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%) upon rotary evaporation.

2'-(Aminooxyethoxy) Nucleoside Amidites

2'-(Aminooxyethoxy) nucleoside amidites (also known in the art as 2'-O-(aminooxyethyl) nucleoside amidites) are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog may be obtained by selective 2'-O-alkylation of diaminopurine riboside. Multigram quantities of diaminopurine riboside may be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside may be resolved and converted to 2'-O-(2-ethylacetyl)guanosine by treatment with adenosine deaminase. (McGee, D. P. C., Cook, P. D., Guinosso, C. J., WO 94/02501 A1 940203.) Standard protection procedures should afford 2'-O-(2-ethylacetyl)-5'-O-(4,4'-dimethoxytrityl)guanosine and 2-N-isobutyryl-6-O-diphenylcarbamoyl-2'-O-(2-ethylacetyl)-5'-O-(4,4'-dimethoxytrityl)guanosine which may be reduced to provide 2-N-isobutyryl-6-O-diphenylcarbamoyl-2'-O-(2-hydroxyethyl)-5'-O-(4,4'-dimethoxytrityl)guanosine. As before the hydroxyl group may be displaced by N-hydroxyphthalimide via a Mitsunobu reaction, and the protected nucleoside may be phosphitylated as usual to yield 2-N-isobutyryl-6-O-diphenylcarbamoyl-2'-O-([2-phthalmidoxy]ethyl)-5'-O-(4,4'-dimethoxytrityl)guanosine-3'-[(2-cyanoethyl)-N,N-diisopropylphosphoramidite].

2'-dimethylaminoethoxyethoxy (2'-DMAEOE)
Nucleoside Amidites

2'-dimethylaminoethoxyethoxy nucleoside amidites (also known in the art as 2'-O-dimethylaminoethoxyethyl, i.e., 2'-O—$CH_2$—O—$CH_2$—$N(CH_3)_2$, or 2'-DMAEOE nucleoside amidites) are prepared as follows. Other nucleoside amidites are prepared similarly.

2'-O-[2(2-N,N-dimethylaminoethoxy)ethyl]-5-methyl Uridine

2[2-(Dimethylamino)ethoxy]ethanol (Aldrich, 6.66 g, 50 mmol) was slowly added to a solution of borane in tetrahydrofuran (1 M, 10 mL, 10 mmol) with stirring in a 100 mL bomb. (Caution: Hydrogen gas evolves as the solid dissolves). $O^2$-,2'-anhydro-5-methyluridine (1.2 g, 5 mmol), and sodium bicarbonate (2.5 mg) were added and the bomb was sealed, placed in an oil bath and heated to 155° C. for 26 h. then cooled to room temperature. The crude solution was concentrated, the residue was diluted with water (200 mL) and extracted with hexanes (200 mL). The product was extracted from the aqueous layer with EtOAc (3×200 mL) and the combined organic layers were washed once with water, dried over anhydrous sodium sulfate, filtered and concentrated. The residue was purified by silica gel column chromatography (eluted with 5:100:2 MeOH/CH$_2$Cl$_2$/TEA) as the eluent. The appropriate fractions were combined and evaporated to afford the product as a white solid.

5'-O-dimethoxytrityl-2'-O-[2(2-N,N-dimethylaminoethoxy) ethyl)]-5-methyl Uridine To 0.5 g (1.3 mmol) of 2'-O-[2(2-N,N-dimethylaminoethoxy)ethyl)]-5-methyl uridine in anhydrous pyridine (8 mL), was added TEA (0.36 mL) and dimethoxytrityl chloride (DMT-Cl, 0.87 g, 2 eq.) and the reaction was stirred for 1 h. The reaction mixture was poured into water (200 mL) and extracted with CH$_2$Cl$_2$ (2×200 mL). The combined CH$_2$Cl$_2$ layers were washed with saturated NaHCO$_3$ solution, followed by saturated NaCl solution, dried over anhydrous sodium sulfate, filtered and evaporated. The residue was purified by silica gel column chromatography (eluted with 5:100:1 MeOH/CH$_2$Cl$_2$/TEA) to afford the product.

5'-O-Dimethoxytrityl-2'-O-[2(2-N,N-dimethylaminoethoxy)-ethyl)]-5-methyl Uridine-3'-O-(cyanoethyl-N,N-diisopropyl)phosphoramidite Diisopropylaminotetrazolide (0.6 g) and 2-cyanoethoxy-N,N-diisopropyl phosphoramidite (1.1 mL, 2 eq.) were added to a solution of 5'-O-dimethoxytrityl-2'-O-[2(2-N,N-dimethylaminoethoxy)ethyl)]-5-methyluridine (2.17 g, 3 mmol) dissolved in CH$_2$Cl$_2$ (20 mL) under an atmosphere of argon. The reaction mixture was stirred overnight and the solvent evaporated. The resulting residue was purified by silica gel column chromatography with EtOAc as the eluent to afford the title compound.

Example 2
Oligonucleotide Synthesis

Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12–16 hr), the oligonucleotides were recovered by precipitating with >3 volumes of ethanol from a 1 M NH$_4$OAc solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or U.S. Pat. No. 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Example 3
Oligonucleoside Synthesis

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 4
PNA Synthesis

Peptide nucleic acids (PNAs) are prepared in accordance with any of the various procedures referred to in Peptide Nucleic Acids (PNA): Synthesis, Properties and Potential Applications, *Bioorganic & Medicinal Chemistry*, 1996, 4, 5–23. They may also be prepared in accordance with U.S. Pat. Nos. 5,539,082, 5,700,922, and 5,719,262, herein incorporated by reference.

Example 5
Synthesis of Chimeric Oligonucleotides

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]—[2'-deoxy]—[2'-O-Me] Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphoramidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia ($NH_4OH$) for 12–16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]—[2'-deoxy]—[2'-O-(Methoxyethyl)] Chimeric Phosphorothioate Oligonucleotides

[2'-O-(2-methoxyethyl)]-[2'-deoxy]-[-2'-O-(methoxyethyl)] chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]—[2'-deoxy Phosphorothioate]—[2'-O-(2-Methoxyethyl) Phosphodiester] Chimeric Oligonucleotides

[2'-O-(2-methoxyethyl phosphodiester]-[2'-deoxy phosphorothioate]-[2'-O-(methoxyethyl) phosphodiester] chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 6

Oligonucleotide Isolation

After cleavage from the controlled pore glass solid support and deblocking in concentrated ammonium hydroxide at 55° C. for 12–16 hours, the oligonucleotides or oligonucleosides are recovered by precipitation out of 1 M $NH_4OAc$ with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (+/−32+/−48). For some studies oligonucleotides were purified by HPLC, as described by Chiang et al., J. Biol. Chem. 1991, 266, 18162–18171. Results obtained with HPLC-purified material were similar to those obtained with non-HPLC purified material.

Example 7

Oligonucleotide Synthesis—96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated $NH_4OH$ at elevated temperature (55–60° C.) for 12–16 hours and the released product then dried in vacuo. The dried product was then re-suspended in sterile water to afford a master plate from which all analytical and test plate samples are then diluted utilizing robotic pipettors.

Example 8

Oligonucleotide Analysis—96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 9

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analysis, cells may be seeded onto 100 mm or other standard tissue culture plates and treated similarly, using appropriate volumes of medium and oligonucleotide.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

MCF7 Cells:

The human breast carcinoma cell line MCF-7 was obtained from the American Type Culture Collection (Manassas, Va.). MCF-7 cells were routinely cultured in DMEM low glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 7000 cells/well for use in RT-PCR analysis.

For Northern blotting or other analyses, cells may be seeded onto 100 mm or other standard tissue culture plates and treated similarly, using appropriate volumes of medium and oligonucleotide.

Treatment with Antisense Compounds:

When cells reached 70% confluency, they were treated with oligonucleotide. For cells grown in 96-well plates, wells were washed once with 100 μL OPTI-MEM™-1 reduced-serum medium (Invitrogen Corporation, Carlsbad, Calif.) and then treated with 130 μL of OPTI-MEM™-1 containing 3.75 μg/mL LIPOFECTIN™ (Invitrogen Corporation, Carlsbad, Calif.) and the desired concentration of oligonucleotide. After 4–7 hours of treatment, the medium was replaced with fresh medium. Cells were harvested 16–24 hours after oligonucleotide treatment.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is ISIS 13920, TCCGTCATCGCTCCTCAGGG, SEQ ID NO: 1, a 2'-O-methoxyethyl gapmer (2'-O-methoxyethyls shown in bold) with a phosphorothioate backbone which is targeted to human H-ras. For mouse or rat cells the positive control oligonucleotide is ISIS 15770, ATGCATTCTGCCCCCAAGGA, SEQ ID NO: 2, a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-Ha-ras (for ISIS 13920) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of H-ras or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 10

Analysis of Oligonucleotide Inhibition of PLML Expression

Antisense modulation of PLML expression can be assayed in a variety of ways known in the art. For example, PLML mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are taught in, for example, Ausubel, F. M. et al., *Current Protocols in Molecular Biology*, Volume 1, pp. 4.1.1–4.2.9 and 4.5.1–4.5.3, John Wiley & Sons, Inc., 1993. Northern blot analysis is routine in the art and is taught in, for example, Ausubel, F. M. et al., *Current Protocols in Molecular Biology*, Volume 1, pp. 4.2.1–4.2.9, John Wiley & Sons, Inc., 1996. Real-time quantitative (PCR) can be conveniently accomplished using the commercially available ABI PRISM™ 7700 Sequence Detection System, available from PE-Applied Biosystems, Foster City, Calif. and used according to manufacturer's instructions.

Protein levels of PLML can be quantitated in a variety of ways well known in the art, such as immunoprecipitation, Western blot analysis (immunoblotting), ELISA or fluorescence-activated cell sorting (FACS). Antibodies directed to PLML can be identified and obtained from a variety of sources, such as the MSRS catalog of antibodies (Aerie Corporation, Birmingham, Mich.), or can be prepared via conventional antibody generation methods. Methods for preparation of polyclonal antisera are taught in, for example, Ausubel, F. M. et al., (*Current Protocols in Molecular Biology*, Volume 2, pp. 11.12.1–11.12.9, John Wiley & Sons, Inc., 1997). Preparation of monoclonal antibodies is taught in, for example, Ausubel, F. M. et al., (*Current Protocols in Molecular Biology*, Volume 2, pp. 11.4.1–11.11.5, John Wiley & Sons, Inc., 1997).

Immunoprecipitation methods are standard in the art and can be found at, for example, Ausubel, F. M. et al., (*Current Protocols in Molecular Biology*, Volume 2, pp. 10.16.1–10.16.11, John Wiley & Sons, Inc., 1998). Western blot (immunoblot) analysis is standard in the art and can be found at, for example, Ausubel, F. M. et al., (*Current Protocols in Molecular Biology*, Volume 2, pp. 10.8.1–10.8.21, John Wiley & Sons, Inc., 1997). Enzyme-linked immunosorbent assays (ELISA) are standard in the art and can be found at, for example, Ausubel, F. M. et al., (*Current Protocols in Molecular Biology*, Volume 2, pp. 11.2.1–11.2.22, John Wiley & Sons, Inc., 1991).

Example 11

Poly(A)+ mRNA Isolation

Poly(A)+ mRNA was isolated according to Miura et al., (*Clin. Chem.*, 1996, 42, 1758–1764). Other methods for poly(A)+ mRNA isolation are taught in, for example, Ausubel, F. M. et al., (*Current Protocols in Molecular Biology*, Volume 1, pp. 4.5.1–4.5.3, John Wiley & Sons, Inc., 1993). Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.

Example 12

Total RNA Isolation

Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QTAVAC™ manifold fitted with a collection tube rack containing 1.2 mL collection tubes. RNA was then eluted by pipetting 170 µL water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 13

Real-Time Quantitative PCR Analysis of PLML mRNA Levels

Quantitation of PLML mRNA levels was determined by real-time quantitative PCR using the ABI PRISM™ 7700 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISMT™ 7700 Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 μL PCR cocktail (2.5×PCR buffer (—MgCl2), 6.6 mM MgCl2, 375 μM each of DATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5×ROX dye) to 96-well plates containing 30 μL total RNA solution. The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent from Molecular Probes. Methods of RNA quantification by RiboGreen™ are taught in Jones, L. J., et al, (Analytical Biochemistry, 1998, 265, 368–374).

In this assay, 170 μL of RiboGreen™ working reagent (RiboGreen™ reagent diluted 1:350 in 10 mM Tris-HCl, 1 mM EDTA, pH 7.5) is pipetted into a 96-well plate containing 30 μL purified, cellular RNA. The plate is read in a CytoFluor 4000 (PE Applied Biosystems) with excitation at 480 nm and emission at 520 nm.

Probes and primers to human PLML were designed to hybridize to a human PLML sequence, using published sequence information (GenBank accession number U28249.1, incorporated herein as SEQ ID NO:3). For human PLML the PCR primers were: forward primer: TTGGGTGGAGGACCGTTCT (SEQ ID NO: 4) reverse primer: AATTCCATCCTGGAGTTCAAGTTT (SEQ ID NO: 5) and the PCR probe was: FAM-TGTCCCCAGGTCCTGTCTCTGCACA-TAMRA (SEQ ID NO: 6) where FAM is the fluorescent dye and TAMRA is the quencher dye. For human GAPDH the PCR primers were: forward primer: GAAGGTGAAGGTCGGAGTC (SEQ ID NO:7) reverse primer: GAAGATGGTGATGG-GATTTC (SEQ ID NO:8) and the PCR probe was: 5' JOE-CAAGCTTCCCGTTCTCAGCC-TAMRA 3' (SEQ ID NO: 9) where JOE is the fluorescent reporter dye and TAMRA is the quencher dye.

Example 14

Northern Blot Analysis of PLML mRNA Levels

Eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™—N+ nylon membranes (Amersham Pharmacia Biotech, Piscataway, N.J.) by overnight capillary transfer using a Northern/Southern Transfer buffer system (TEL-TEST "B" Inc., Friendswood, Tex.). RNA transfer was confirmed by UV visualization. Membranes were fixed by UV cross-linking using a STRATALINKER™ UV Crosslinker 2400 (Stratagene, Inc, La Jolla, Calif.) and then probed using QUICKHYB™ hybridization solution (Stratagene, La Jolla, Calif.) using manufacturer's recommendations for stringent conditions.

To detect human PLML, a human PLML specific probe was prepared by PCR using the forward primer TTGGGTG-GAGGACCGTTCT (SEQ ID NO: 4) and the reverse primer AATTCCATCCTGGAGTTCAAGTTT (SEQ ID NO: 5). To normalize for variations in loading and transfer efficiency membranes were stripped and probed for human glyceraldehyde-3-phosphate dehydrogenase (GAPDH) RNA (Clontech, Palo Alto, Calif.).

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 15

Antisense Inhibition of Human PLML Expression by Chimeric Phosphorothioate Oligonucleotides Having 2'-MOE Wings and a Deoxy Gap In accordance with the present invention, a series of oligonucleotides were designed to target different regions of the human PLML RNA, using published sequences (GenBank accession number U28249.1, incorporated herein as SEQ ID NO: 3, GenBank accession number X93036.1, incorporated herein as SEQ ID NO: 10, and GenBank accession number AA133749.1, incorporated herein as SEQ ID NO: 11). The oligonucleotides are shown in Table 1. "Target site" indicates the first (5'-most) nucleotide number on the particular target sequence to which the oligonucleotide binds. All compounds in Table 1 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines. The compounds were analyzed for their effect on human PLML mRNA levels by quantitative real-time PCR as described in other examples herein. Data are averages from two experiments in which MCF7 cells were treated with the antisense oligonucleotides of the present invention. If present, "N.D." indicates "no data".

TABLE 1

Inhibition of human PLML mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 138502 | 5'UTR | 3 | 2 | ttgctggcagttgtggagaa | 4 | 12 |
| 138503 | Coding | 11 | 12 | cttgccgctggtacaatttc | 0 | 13 |

TABLE 1-continued

Inhibition of human PLML mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 138504 | 5'UTR | 3 | 16 | gcctggtggaaggattgctg | 18 | 14 |
| 138505 | 5'UTR | 3 | 30 | agatgatgtgttttgcctgg | 7 | 15 |
| 138506 | 5'UTR | 10 | 35 | agcgctggcctgtgtggttc | 76 | 16 |
| 138507 | Coding | 11 | 37 | cttaaagtcccttccaggc | 0 | 17 |
| 138508 | 5'UTR | 3 | 65 | tgccacgccctaagcaaacc | 0 | 18 |
| 138509 | 5'UTR | 3 | 69 | aagctgccacgccctaagca | 0 | 19 |
| 138510 | 5'UTR | 3 | 82 | ctgcgtttatccgaagctgc | 0 | 20 |
| 138511 | 5'UTR | 3 | 85 | gtcctgcgtttatccgaagc | 12 | 21 |
| 138512 | 5'UTR | 3 | 88 | ggagtcctgcgtttatccga | 30 | 22 |
| 138513 | 5'UTR | 3 | 94 | ccaggcggagtcctgcgttt | 17 | 23 |
| 138514 | 5'UTR | 3 | 120 | cagaggttccgggagaaatc | 61 | 24 |
| 138515 | 5'UTR | 3 | 138 | gtggttcaccaggctgagca | 77 | 25 |
| 138516 | 5'UTR | 3 | 143 | cctgtgtggttcaccaggct | 86 | 26 |
| 138517 | 5'UTR | 3 | 148 | tcgggcctgtgtggttcacc | 64 | 27 |
| 138518 | 5'UTR | 3 | 152 | aaactcgggcctgtgtggtt | 62 | 28 |
| 138519 | 5'UTR | 3 | 188 | taagccgcagctgcaccgtg | 60 | 29 |
| 138520 | coding | 11 | 207 | gagcgctggcctgtgtggtt | 70 | 30 |
| 138521 | Coding | 10 | 223 | gcattttgcactcatgacga | 75 | 31 |
| 138522 | Start Codon | 3 | 251 | accttctgcatgtcagagcg | 76 | 32 |
| 138523 | Coding | 3 | 296 | tccaggacaggaaagcctgc | 55 | 33 |
| 138524 | Coding | 3 | 344 | tgccagtcatagtagaaagg | 57 | 34 |
| 138525 | Coding | 3 | 366 | gcagatgagcccgccaacct | 72 | 35 |
| 138526 | Coding | 3 | 371 | ccagcgcagatgagcccgcc | 73 | 36 |
| 138527 | Coding | 3 | 397 | tgatgatgcccatggcgcac | 74 | 37 |
| 138528 | Coding | 3 | 405 | catgacgatgatgatgccca | 71 | 38 |
| 138529 | Coding | 3 | 415 | tccactcactcatgacgatg | 62 | 39 |
| 138530 | Coding | 3 | 507 | aaacttgcatttgcattttg | 68 | 40 |
| 138531 | Coding | 3 | 519 | ggacttctggccaaacttgc | 79 | 41 |
| 138532 | Coding | 3 | 521 | ccggacttctggccaaactt | 87 | 42 |
| 138533 | Coding | 3 | 531 | tggatggtgaccggacttct | 57 | 43 |
| 138534 | Coding | 3 | 544 | gtggagtctcccctggatgg | 82 | 44 |
| 138535 | Coding | 3 | 552 | gatgagaggtggagtctccc | 55 | 45 |
| 138536 | Stop Codon | 3 | 585 | ctgtcctcatcagctttggg | 66 | 46 |
| 138537 | 3'UTR | 3 | 605 | tccacccaatttcagctggt | 87 | 47 |
| 138538 | 3'UTR | 3 | 650 | tcaagtttctgtgcagagac | 85 | 48 |

TABLE 1-continued

Inhibition of human PLML mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 138539 | 3'UTR | 3 | 682 | ccagcagaggaggaagaatt | 75 | 49 |
| 138540 | 3'UTR | 3 | 694 | tgcaaaggagtcccagcaga | 93 | 50 |
| 138541 | 3'UTR | 3 | 711 | gagatgaggccctgccatgc | 87 | 51 |
| 138542 | 3'UTR | 3 | 716 | gaggtgagatgaggccctgc | 82 | 52 |
| 138543 | 3'UTR | 3 | 738 | gaacaaagagaccctcttgc | 86 | 53 |
| 138544 | 3'UTR | 3 | 742 | aattgaacaaagagaccctc | 66 | 54 |
| 138545 | 3'UTR | 3 | 767 | ggcacaatcattttagataa | 82 | 55 |
| 138546 | 3'UTR | 3 | 775 | tgggcagaggcacaatcatt | 87 | 56 |
| 138547 | 3'UTR | 3 | 780 | ctgcttgggcagaggcacaa | 83 | 57 |
| 138548 | 3'UTR | 3 | 809 | ccccaatgcacacataggaa | 57 | 58 |
| 138549 | 3'UTR | 3 | 850 | ctccagggcacgccaacctt | 51 | 59 |
| 138550 | 3'UTR | 3 | 873 | tcagtgccagcctctgtgtc | 17 | 60 |
| 138551 | 3'UTR | 3 | 876 | ggctcagtgccagcctctgt | 51 | 61 |
| 138552 | 3'UTR | 3 | 915 | ccacaagggaacaggcctgt | 42 | 62 |
| 138553 | 3'UTR | 3 | 927 | ccatgtcccaagccacaagg | 23 | 63 |
| 138554 | 3'UTR | 3 | 970 | catatgaggtcccatggctg | 31 | 64 |
| 138555 | 3'UTR | 3 | 974 | attgcatatgaggtcccatg | 42 | 65 |
| 138556 | 3'UTR | 3 | 983 | aaatcccaaattgcatatga | 50 | 66 |
| 138557 | 3'UTR | 3 | 993 | ggctactagtaaatcccaaa | 58 | 67 |
| 138558 | 3'UTR | 3 | 998 | cttttggctactagtaaatc | 24 | 68 |
| 138559 | 3'UTR | 3 | 1030 | gtgttccatctggttagagc | 36 | 69 |
| 138560 | 3'UTR | 3 | 1050 | gggtccactggaatgttcca | 64 | 70 |
| 138561 | 3'UTR | 3 | 1055 | gtccagggtccactggaatg | 37 | 71 |
| 138562 | 3'UTR | 3 | 1063 | ctggaatggtccagggtcca | 56 | 72 |
| 138563 | 3'UTR | 3 | 1077 | atgtcccagttttcctggaa | 46 | 73 |
| 138564 | 3'UTR | 3 | 1101 | cttccatcatagcgggacga | 51 | 74 |
| 138565 | 3'UTR | 3 | 1114 | aactgtctgaacacttccat | 44 | 75 |
| 138566 | 3'UTR | 3 | 1124 | tactattataaactgtctga | 34 | 76 |
| 138567 | 3'UTR | 3 | 1148 | gtaagtgagagggtcacagg | 41 | 77 |
| 138568 | 3'UTR | 3 | 1173 | tcttgtaataaagtgaggtc | 47 | 78 |
| 138569 | 3'UTR | 3 | 1228 | gtagcatagggaattattta | 40 | 79 |
| 138570 | 3'UTR | 3 | 1249 | ggtcattgtatgttattaag | 45 | 80 |
| 138571 | 3'UTR | 3 | 1293 | gtctcaagggactttgaggc | 56 | 81 |
| 138572 | 3'UTR | 3 | 1327 | agaacatttcgcatgcctta | 66 | 82 |
| 138573 | 3'UTR | 3 | 1330 | atgagaacatttcgcatgcc | 52 | 83 |
| 138574 | 3'UTR | 3 | 1367 | gggtgttttgagttttaggc | 48 | 84 |

TABLE 1-continued

Inhibition of human PLML mRNA levels by chimeric phosphorothioate oligonucleotides having 2'-MOE wings and a deoxy gap

| ISIS # | REGION | TARGET SEQ ID NO | TARGET SITE | SEQUENCE | % INHIB | SEQ ID NO |
|---|---|---|---|---|---|---|
| 138575 | 3'UTR | 3 | 1396 | tgtctcaggacattggagga | 33 | 85 |
| 138576 | 3'UTR | 3 | 1401 | gttcatgtctcaggacattg | 51 | 86 |
| 138577 | 3'UTR | 3 | 1407 | ttttgggttcatgtctcagg | 54 | 87 |
| 138578 | 3'UTR | 3 | 1430 | tcacgagtttattgtgggtc | 35 | 88 |
| 138579 | 3'UTR | 3 | 1435 | acaagtcacgagtttattgt | 37 | 89 |

As shown in Table 1, SEQ ID NOs 16, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 61, 67, 70, 72, 74, 81, 82, 83, 86 and 87 demonstrated at least 51% inhibition of human PLML expression in this assay and are therefore preferred. The target sites to which these preferred sequences are complementary are herein referred to as "preferred target regions" and are therefore preferred sites for targeting by compounds of the present invention.

TABLE 2

Sequence and position of preferred target regions identified in PLML.

| SITEID | TARGET SEQ ID NO | TARGET SITE | SEQUENCE | REV COMP OF SEQ ID | ACTIVE IN | SEQ ID NO |
|---|---|---|---|---|---|---|
| 51559 | 10 | 35 | gaaccacacaggccagcgct | 16 | H. sapiens | 90 |
| 51570 | 3 | 120 | gatttctcccggaacctctg | 24 | H. sapiens | 91 |
| 51571 | 3 | 138 | tgctcagcctggtgaaccac | 25 | H. sapiens | 92 |
| 51572 | 3 | 143 | agcctggtgaaccacacagg | 26 | H. sapiens | 93 |
| 51573 | 3 | 148 | ggtgaaccacacaggcccga | 27 | H. sapiens | 94 |
| 51574 | 3 | 152 | aaccacacaggcccgagttt | 28 | H. sapiens | 95 |
| 51575 | 3 | 188 | cacggtgcagctgcggctta | 29 | H. sapiens | 96 |
| 51636 | 11 | 207 | aaccacacaggccagcgctc | 30 | H. sapiens | 97 |
| 51560 | 10 | 223 | tcgtcatgagtgcaaaatgc | 31 | H. sapiens | 98 |
| 51576 | 3 | 251 | cgctctgacatgcagaaggt | 32 | H. sapiens | 99 |
| 51577 | 3 | 296 | gcaggctttcctgtcctgga | 33 | H. sapiens | 100 |
| 51578 | 3 | 344 | cctttctactatgactggca | 34 | H. sapiens | 101 |
| 51579 | 3 | 366 | aggttggcgggctcatctgc | 35 | H. sapiens | 102 |
| 51580 | 3 | 371 | ggcgggctcatctgcgctgg | 36 | H. sapiens | 103 |
| 51581 | 3 | 397 | gtgcgccatgggcatcatca | 37 | H. sapiens | 104 |
| 51582 | 3 | 405 | tgggcatcatcatcgtcatg | 38 | H. sapiens | 105 |
| 51583 | 3 | 415 | catcgtcatgagtgagtgga | 39 | H. sapiens | 106 |

TABLE 2-continued

Sequence and position of preferred target regions identified in PLML.

| SITEID | TARGET SEQ ID NO | TARGET SITE | SEQUENCE | REV COMP OF SEQ ID | ACTIVE IN | SEQ ID NO |
|---|---|---|---|---|---|---|
| 51584 | 3 | 507 | caaaatgcaaatgcaagttt | 40 | H. sapiens | 107 |
| 51585 | 3 | 519 | gcaagtttggccagaagtcc | 41 | H. sapiens | 108 |
| 51586 | 3 | 521 | aagtttggccagaagtccgg | 42 | H. sapiens | 109 |
| 51587 | 3 | 531 | agaagtccggtcaccatcca | 43 | H. sapiens | 110 |
| 51588 | 3 | 544 | ccatccaggggagactccac | 44 | H. sapiens | 111 |
| 51589 | 3 | 552 | gggagactccacctctcatc | 45 | H. sapiens | 112 |
| 51590 | 3 | 585 | cccaaagctgatgaggacag | 46 | H. sapiens | 113 |
| 51591 | 3 | 605 | accagctgaaattgggtgga | 47 | H. sapiens | 114 |
| 51592 | 3 | 650 | gtctctgcacagaaacttga | 48 | H. sapiens | 115 |
| 51593 | 3 | 682 | aattcttcctcctctgctgg | 49 | H. sapiens | 116 |
| 51594 | 3 | 694 | tctgctgggactcctttgca | 50 | H. sapiens | 117 |
| 51595 | 3 | 711 | gcatggcagggcctcatctc | 51 | H. sapiens | 118 |
| 51596 | 3 | 716 | gcagggcctcatctcacctc | 52 | H. sapiens | 119 |
| 51597 | 3 | 738 | gcaagagggtctcttcgttc | 53 | H. sapiens | 120 |
| 51598 | 3 | 742 | gagggtctctttgttcaatt | 54 | H. sapiens | 121 |
| 51599 | 3 | 767 | ttatctaaaatgattgtgcc | 55 | H. sapiens | 122 |
| 51600 | 3 | 775 | aatgattgtgcctctgccca | 56 | H. sapiens | 123 |
| 51601 | 3 | 780 | ttgtgcctctgcccaagcag | 57 | H. sapiens | 124 |
| 51602 | 3 | 809 | ttcctatgtgtgcattgggg | 58 | H. sapiens | 125 |
| 51603 | 3 | 850 | aaggttggcgtgccctggag | 59 | H. sapiens | 126 |
| 51605 | 3 | 876 | acagaggctggcactgagcc | 61 | H. sapiens | 127 |
| 51611 | 3 | 993 | tttgggatttactagtagcc | 67 | H. sapiens | 128 |
| 51614 | 3 | 1050 | tggaacattccagtggaccc | 70 | H. sapiens | 129 |
| 51616 | 3 | 1063 | tggaccctggaccattccag | 72 | H. sapiens | 130 |
| 51618 | 3 | 1101 | tcgtcccgctatgatggaag | 74 | H. sapiens | 131 |
| 51625 | 3 | 1293 | gcctcaaagtcccttgagac | 81 | H. sapiens | 132 |
| 51626 | 3 | 1327 | taaggcatgcgaaatgttct | 82 | H. sapiens | 133 |
| 51627 | 3 | 1330 | ggcatgcgaaatgttctcat | 83 | H. sapiens | 134 |
| 51630 | 3 | 1401 | caatgtcctgagacatgaac | 86 | H. sapiens | 135 |
| 51631 | 3 | 1407 | cctgagacatgaacccaaaa | 87 | H. sapiens | 136 |

As these "preferred target regions" have been found by experimentation to be open to, and accessible for, hybridization with the antisense compounds of the present invention, one of skill in the art will recognize or be able to ascertain, using no more than routine experimentation, further embodiments of the invention that encompass other compounds that specifically hybridize to these sites and consequently inhibit the expression of PLML.

Example 16

Western Blot Analysis of PLML Protein Levels

Western blot analysis (immunoblot analysis) is carried out using standard methods. Cells are harvested 16–20 h after oligonucleotide treatment, washed once with PBS, suspended in Laemmli buffer (100 ul/well), boiled for 5 minutes and loaded on a 16% SDS-PAGE gel. Gels are run for 1.5 hours at 150 V, and transferred to membrane for western blotting. Appropriate primary antibody directed to PLML is used, with a radiolabeled or fluorescently labeled secondary antibody directed against the primary antibody species. Bands are visualized using a PHOSPHORIMAGER™ (Molecular Dynamics, Sunnyvale Calif.).

What is claimed is:

1. An antisense oligonucleotide 8 to 80 nucleobases in length targeted to nucleobases 694 through 799 of a 3'-untranslated region of a nucleic acid molecule encoding human PLML (SEQ ID NO: 3), wherein said antisense oligonucleotide specifically hybridizes with said region of said nucleic acid molecule encoding human PLML.

2. The antisense oligonucleotide of claim 1 which comprises at least one modified internucleoside linkage.

3. The antisense oligonuclootide of claim 2 wherein the modified internucleoside linkage is a phosphorothioate linkage.

4. The antisense oligonucleotide of claim 1 which comprises at least one modified sugar moiety.

5. The antisense oligonucleotide of claim 4 wherein the modified sugar moiety is a 2-o-methoxyethyl sugar moiety.

6. The antiseniseoligonucleotide of claim 1 which comprises at least one modified nucleobase.

7. The antisense oligonucleotide of clai 6 wherein the modified nucleobase is a 5-methylcytosine.

8. The antisense oligonucleotide of claim 1 which is a chimeric oligonucleotide.

9. A composition comprising the antisense oligonucleoticie of claim 1 and a pharmaceutically acceptable carrier or diluent.

10. The composition of claim 9 further comprising a colloidal dispersion system.

* * * * *

UNITED STATES PATENT AND TRADEMARK OFFICE
CERTIFICATE OF CORRECTION

| | |
|---|---|
| PATENT NO. | : 6,825,337 B2 |
| APPLICATION NO. | : 10/160792 |
| DATED | : November 30, 2004 |
| INVENTOR(S) | : Andrew T. Watt |

It is certified that error appears in the above-identified patent and that said Letters Patent is hereby corrected as shown below:

Column 102, Claim 6, line 14, please delete "antiseniseoligonucleotide" and insert therefor -- antisense oligonucleotide --;

Column 102, Claim 7, line 16, please delete "clai" and insert therefor -- claim --;

Column 102, Claim 9, lines 20-21, please delete "oligonucleoticie" and insert therefor -- oligonucleotide --.

Signed and Sealed this

Eighteenth Day of September, 2007

JON W. DUDAS
*Director of the United States Patent and Trademark Office*